United States Patent
Shapiro et al.

(10) Patent No.: US 9,719,084 B2
(45) Date of Patent: Aug. 1, 2017

(54) CO-TRANSCRIPTIONAL ASSEMBLY OF MODIFIED RNA NANOPARTICLES

(71) Applicants: The United States of America, as represented by the Secretary, Department of Health & Human Services, Washington, DC (US); The Regents of the University of California, Oakland, CA (US)

(72) Inventors: Bruce A. Shapiro, Gaithersburg, MD (US); Kirill A. Afonin, Charlotte, NC (US); Maria L. Kireeva, Gaithersburg, MD (US); Mikhail Kashlev, Frederick, MD (US); Luc Jaeger, Goleta, CA (US); Wade W. Grabow, Shoreline, WA (US)

(73) Assignees: The United States of America, as represented by the Secretary, Department of Health & Human Services, Washington, DC (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 14/426,707

(22) PCT Filed: Sep. 6, 2013

(86) PCT No.: PCT/US2013/058492
§ 371 (c)(1),
(2) Date: Mar. 6, 2015

(87) PCT Pub. No.: WO2014/039809
PCT Pub. Date: Mar. 13, 2014

(65) Prior Publication Data
US 2015/0203842 A1   Jul. 23, 2015

Related U.S. Application Data

(60) Provisional application No. 61/698,227, filed on Sep. 7, 2012.

(51) Int. Cl.
C12P 19/34 (2006.01)
C12N 15/11 (2006.01)

(52) U.S. Cl.
CPC .......... *C12N 15/111* (2013.01); *C12P 19/34* (2013.01); *C12N 2310/14* (2013.01); *C12N 2310/33* (2013.01); *C12N 2310/3519* (2013.01); *C12N 2310/51* (2013.01); *C12N 2310/52* (2013.01); *C12N 2320/32* (2013.01); *C12N 2330/50* (2013.01)

(58) Field of Classification Search
None
See application file for complete search history.

(56) References Cited

U.S. PATENT DOCUMENTS

2004/0171047 A1* 9/2004 Dahl .................... C12Q 1/6865
435/5
2010/0120024 A1   5/2010 Cload et al.

OTHER PUBLICATIONS

Lapham RNA 2:289-296, 1996.*
Grabow Wade W et al: "Self-assembling RNA nanorings based on RNAI/II inverse kissing complexes.", Nano Letters Feb. 9, 2011, vol. 11, No. 2, Feb. 9, 2011 (Feb. 9, 2011), pp. 878-887, XP002721906, ISSN: 1530-6992 the whole document.
Afonin Kirill A et al: "Design and self-assembly of siRNA-functionalized RNA nanoparticles for use in automated nanomedicine.", Nature Protocols Dec. 2011, vol. 6, No. 12, Dec. 2011 (Dec. 2011), pp. 2022-2034, XP009177058, ISSN: 1750-2799 the whole document.
Gopalakrishna Sailesh et al: "Template-dependent incorporation of 8-N3AMP into RNA with bacteriophage T7 RNA polymerase", RNA (Cold Spring Harbor), vol. 10, No. 11, Nov. 2004 (Nov. 2004), pp. 1820-1830, XP002721908, ISSN: 1355-8382 the whole document.
Afonin Kirill A et al: "Co-transcriptional assembly of chemically modified RNA nanoparticles functionalized with siRNAs.", Nano Letters Oct. 10, 2012, vol. 12, No. 10, Oct. 10, 2012 (Oct. 10, 2012), pp. 5192-5195, XP002721909, ISSN: 1530-6992 the whole document.
International Search Report from International Application PCT/2013/058492 dated Apr. 8, 2014.

* cited by examiner

*Primary Examiner* — Nancy Treptow
(74) *Attorney, Agent, or Firm* — Locke Lord LLP; Gabriel J. McCool

(57) ABSTRACT

A method is provided for generating RNA nanoparticles having modified nucleotides and/or having increased nuclease resistance where the RNA nanoparticles are formed cotranscriptionally by T7 RNA polymerase in the presence of manganese ions.

10 Claims, 11 Drawing Sheets

CO-TRANSCRIPTIONAL ASSEMBLY OF MODIFIED RNA NANOPARTICLES

RELATED APPLICATIONS

This application is a national state entry of International Application No. PCT/US13/58492 having an international filing date of Sep. 6, 2013, which claims priority to U.S. Provisional Application No. 61/698,227, filed Sep. 7, 2012, the entireties of which are incorporated herein by reference.

STATEMENT OF RIGHTS TO INVENTIONS MADE UNDER FEDERALLY SPONSORED RESEARCH

This work was supported by the National Institutes of Health. The U.S. Government has certain rights in the invention.

SEQUENCE LISTING

The instant application contains a Sequence Listing which has been submitted electronically in ASCII format and is hereby incorporated by reference in its entirety. Said ASCII copy, created on May 18, 2016, is named 1420378.405US9_SL.txt and is 12,869 bytes in size.

BACKGROUND OF THE INVENTION

RNA molecules can be designed to form a wide variety of compact and thermodynamically stable three-dimensional structures (nanoparticles or NP) suitable for a broad range of nanotechnological and biomedical applications. Currently, two main strategies are used to design various RNA NP. In one strategy, based on the principles of RNA architectonics the single-stranded RNAs (ssRNAs) form monomers with pre-folded structural motifs followed by bottom-up assemblies via intermolecular tertiary hydrogen bond formations (e.g. hexameric nanorings). In another strategy, ssRNAs are designed to avoid stable internal secondary structures, and their assemblies are built solely from intermolecular interactions independent of any tertiary bindings (e.g. nanocubes). Fusion of the individual RNAs participating in NP formation with functional/therapeutic RNAs (ribozymes, small interfering RNA (siRNAs), aptamers, etc) allows precise control over the stoichiometric organization and simultaneous delivery of different RNA functionalities into cells. However, biomedical integration of such functional RNA NP is somewhat limited by at least three obstacles:

(i) The Cost and Size Limitations Associated with Chemical Synthesis of RNA.

The addition of functional groups to RNA scaffolds typically involves increasing the length of the individual RNA strands entering into the composition of the RNA nanoparticles. This strategy often requires the synthesis of RNAs in lengths that exceed what is currently available by commercial synthesis (i.e. RNAs that are greater than 60-nt). Furthermore, because chemical synthesis of RNA is relatively expensive compared to DNA, long RNAs are usually prepared by in vitro transcription with bacteriophage T7 RNA polymerase.

(ii) The Complexity of RNA NP Production.

Given that the synthesis of DNA oligos are relatively inexpensive, RNA synthesis usually relies on the use of DNA templates coding individual strands of RNA NP which are transcribed in vitro. Resulting RNAs are gel purified, recovered from purification and combined at equimolar quantities. Thermal denaturation and specific refolding protocols are used to ensure the desired NP formation. Denaturation and refolding conditions strongly depend on NP design strategies as well as the sequences of individual RNAs. Therefore, each NP requires an optimization of the assembly protocol.

(iii) Low Retention Time of RNA NP in the Patient Blood Stream Due to their Susceptibility to Nuclease Degradation.

Inclusion of dNMPs chemically modified at the 2'-position of the ribose sugar into the RNA strands of RNA NPs offers a promising way to increase the retention time of functional RNA NPs in the blood stream. Production of chemically modified RNA NPs has been previously achieved through transcription of individual RNA strands by mutant bacteriophage T7 RNA polymerase in the presence of 2'-fluorinated dUTP, and unmodified ATP, GTP, and CTP. This Y639F mutant enzyme (defective in discrimination between rNTP and dNTP substrates) is commercially available and relatively expensive. The purified RNA strands were used for NP assemblies by thermal denaturation and refolding. Notably, the overall yields of fluorinated RNAs, produced by the mutant polymerase according to the manufacturer's protocol, are significantly lower than the amount of unmodified transcripts (data not shown), precluding the large-scale production of chemically modified NPs. Apparently, the enzyme mutation does not completely alleviate the inefficient incorporation of several modified residues in a row, which sometimes is essential for formation of the full-length transcript.

Accordingly, improved methods of producing RNA nanoparticles are needed

SUMMARY OF THE INVENTION

As described below, the present invention features methods of producing RNA nanoparticle having modified nucleotides using wild-type T7 RNA polymerase in a manganese containing buffer.

In one aspect, the invention generally features a method of producing modified RNA nanoparticles involving mixing one or more dsDNA templates, wild-type T7 RNA polymerase, a modified nucleotide, and a buffer comprising manganese ions, and incubating the mixture, thereby co-transcriptionally forming RNA nanoparticles having modified nucleotide.

In another aspect, the invention generally features a method of incorporating modified nucleotides into an RNA involving mixing one or more dsDNA templates, wild-type T7 RNA polymerase, a modified nucleotide, and a buffer comprising manganese ions, and incubating the mixture, thereby incorporating modified nucleotides into the RNA.

In yet another aspect, the invention generally features a method of generating modified RNA involving mixing one or more dsDNA templates, wild-type T7 RNA polymerase, a modified nucleotide, and a buffer comprising manganese ions, and incubating the mixture, thereby generating modified RNA.

In a further aspect, the invention generally features a method of generating a nuclease resistant RNA nanoparticles involving mixing one or more dsDNA templates, wild-type T7 RNA polymerase, a modified nucleotide, and a buffer comprising manganese ions, and incubating the mixture, thereby generating nuclease resistant RNA.

In various embodiments of any of the above aspects or any other aspect of the invention delineated herein, the method further comprises RNAse H treatment.

In various embodiments of any of the above aspects or any other aspect of the invention delineated herein, the manganese ions are at from 0.25 mM to 0.75 mM. In another embodiment, the manganese ions are at about 0.5 mM. In yet another embodiment the modified RNA nanoparticles comprise a plurality of distinct RNA strands. In another embodiment the modified RNA nanoparticles comprise between 12 and 22 distinct RNA strands. In further embodiments the modified nucleotide comprises a modified nucleoside selected from the group consisting of 5-methylcytidine, 5-methyluridine, 2-thiouridine, $m^1A$ (1-methyladenosine); $m^2A$ (2-methyladenosine); Am (2'-O-methyladenosine); $ms^2 m^6A$ (2-methylthio-$N^6$-methyladenosine); $i^6A$ ($N^6$-isopentenyladenosine); $ms^2i6A$ (2-methylthio-$N^6$ isopentenyladenosine); $io^6A$ ($N^6$-(cis-hydroxyisopentenyl)adenosine); $ms^2i^6A$ (2-methylthio-$N^6$-(cis-hydroxyisopentenyl)adenosine); $g^6A$ ($N^6$-glycinylcarbamoyladenosine); $t^6A$ ($N^6$-threonylcarbamoyladenosine); $ms^2t^6$ A (2-methylthio-$N^6$-threonyl carbamoyladenosine); ($N^6$-methyl-$N^6$-threonylcarbamoyladenosine); $hn^6A$($N^6$-hydroxynorvalylcarbamoyladenosine); $ms^2hn^6A$ (2-methylthio-$N^6$-hydroxynorvalyl carbamoyladenosine); Ar(p) (2'-O-ribosyladenosine (phosphate)); I (inosine); $m^1I$ (1-methylinosine); $m^1Im$ (1,2'-O-dimethylinosine); $m^3C$ (3-methylcytidine); Cm (2'-O-methylcytidine); $s^2C$ (2-thiocytidine); $ac^4C$(N4-acetylcytidine); $f^5C$ (5-formylcytidine); $m^5$ Cm (5,2'-O-dimethylcytidine); $ac^4Cm$ ($N^4$-acetyl-2'-O-methylcytidine); $k^2C$ (lysidine); m1G (1-methylguanosine); $m^2G$ (N2-methylguanosine); $m^7G$ (7-methylguanosine); Gm (2'-O-methylguanosine); $m^2{}_2G$ dimethylguanosine); $m^2Gm$ ($N^2$,2'-O-dimethylguanosine); $m^2{}_2Gm$ ($N^2$,$N^2$,2'-O-trimethylguanosine); Gr(p) (2'-O-ribosylguanosine (phosphate)); yW (wybutosine); $o_2yW$ (peroxywybutosine); OHyW (hydroxywybutosine); OHyW* (undermodified hydroxywybutosine); imG (wyosine); mimG (methylwyosine); Q (queuosine); oQ (epoxyqueuosine); galQ (galactosyl-queuosine); manQ (mannosyl-queuosine); $preQ_0$ (7-cyano-7-deazaguanosine); $preQ_1$ (7-aminomethyl-7-deazaguanosine); $G^+$ (archaeosine); D (dihydrouridine); $m^5Um$ (5,2'-O-dimethyluridine); $s^4U$ (4-thiouridine); $m^5s2U$ (5-methyl-2-thiouridine); $s^2Um$ (2-thio-2'-O-methyluridine); $acp^3U$ (3-(3-amino-3-carboxypropyl)uridine); $ho^5U$ (5-hydroxyuridine); $mo^5U$ (5-methoxyuridine); $cmo^5U$ (uridine 5-oxyacetic acid); $mcmo^5U$ (uridine 5-oxyacetic acid methyl ester); $chm^5U$ (5-(carboxyhydroxymethyl)uridine)); $mchm^5U$ (5-(carboxyhydroxymethyl)uridine methyl ester); $mcm^5U$ (5-methoxycarbonylmethyluridine); $mcm^5Um$ (5-methoxycarbonylmethyl-2'-O-methyluridine); $mcm^5s^2U$ (5-methoxycarbonylmethyl-2-thiouridine); $nm^5s2U$ (5-aminomethyl-2-thiouridine); $mnm^5U$ (5-methylaminomethyluridine); $mnm^5s^2U$ (5-methylaminomethyl-2-thiouridine); $mnm^5se2U$ (5-methylaminomethyl-2-selenouridine); $ncm^5U$ (5-carbamoylmethyluridine); $ncm^5Um$ (5-carbamoylmethyl-2'-O-methyluridine); $cmnm^5U$ (5-carboxymethylaminomethyluridine); $cmnm^5Um$ (5-carboxymethylaminomethyl-2'-O-methyluridine); $cmnm^5s2U$ (5-carboxymethylaminomethyl-2-thiouridine); $m6_2A$ ($N^6$, $N^6$-dimethyladenosine); Im (2'-O-methylinosine); $m^4C$(N4-methylcytidine); $m^4$ Cm ($N^4$,2'-O-dimethylcytidine); $hm^5C$ (5-hydroxymethylcytidine); $m^3U$ (3-methyluridine); $cm^5U$ (5-carboxymethyluridine); $m^6Am$ (N6,2'-O-dimethyladenosine); $m^6{}_2Am$ ($N^6$,$N^6$,O-2'-trimethyladenosine); $m^2{,}7G$ ($N^2$,7-dimethylguanosine); $m^2{,}2{,}7G$ ($N^2$,N2,7-trimethylguanosine); $m^3Um$ (3,2'-O-dimethyluridine); $m^5D$ (5-methyldihydrouridine); $f^5Cm$ (5-formyl-2'-O-methylcytidine); $m^1Gm$ (1,2'-O-dimethylguanosine); $m^1Am$ (1,2'-dimethyladenosine); $\tau m^5U$ (5-taurinomethyluridine); $\tau m^5s2U$ (5-taurinomethyl-2-thiouridine)); imG-14 (4-demethylwyosine); imG2 (isowyosine); and $ac^6A$ (N6-acetyladenosine). In other embodiments the modified nucleotide is selected from the group consisting of 2'-fluoro-dUMP, 2'-fluoro-dCMP, 2'-fluoro-dGMP, 2'-fluoro-dAMP, and 8-$N_3$AMP. In additional embodiments the modified nucleotide is 2'-fluoro-dUTP. In yet another embodiment the nuclease resistant RNA has increased serum half-life compared to a corresponding wild-type RNA.

DEFINITIONS

As used herein, a "modified nucleoside" is a nucleoside that has one or more chemical structures covalently attached which are not commonly found in naturally occurring nucleosides. A "modified nucleotide" is a modified nucleoside with one to three phosphate groups attached.

As used herein, a "nuclease resistant RNA" is an RNA molecule having one or more modified nucleotides that confer resistance to degradation by nucleases.

As used herein, a "composition" refers to the combination of an active agent (e.g., a polyvalent RNA nanoparticle). The composition additionally can comprise a pharmaceutically acceptable carrier or excipient and/or one or more therapeutic agents for use in vitro or in vivo.

As used herein, the term "hairpin loop" is meant to refer to a feature of ribonucleic acid (RNA) secondary structure. A hairpin loop occurs when RNA folds back on itself. Base pairing along the double-stranded stems may be either perfectly complementary or may contain mismatches.

As used herein, the term "kissing loop" is meant to refer to the base-pairing formed by complementary sequences in the apical loops of two hairpins which is a basic type of RNA tertiary contact.

As used herein, the term "nanoparticle" is meant to refer to a particle between 10 nm and 200 nm in size. A nanoparticle according to the invention comprises a ribonucleic acid (RNA). The RNA can be obtained from any source, for example bacteriophages phi 29, HIV, *Drosophila*, the ribosome, or be a synthetic RNA.

As used herein, the term "nanotube" is meant to refer to the assembly of nanoparticles from RNA into a two or three dimensional structure. The assembly of nano-particles in to nanotubes can be by a process of self-assembly. Self-assembly can occur by ligation, chemical conjugation, covalent linkage, and non-covalent interactions of RNA, especially in the formation of RNA multimeric complexes.

As used herein, the term "motif" in reference to a nanoparticle is meant to refer to a double-stranded or single-stranded ribonucleic acid or analog thereof. Individual motifs are joined together into larger particles by attachment to each other. Attachment can occur by non-covalent linking.

The term "tectosquares" as used herein is meant to refer to a nanoparticle comprised of four different tectoRNA units. A tectosquare can refer to a square shaped tetramer. In preferred embodiments, the RNA units self-assemble to form a square-shaped nanoparticle, where the interactions are preferably through four non-covalent loop-loop interactions. In further embodiments, the non-covalent interactions are distinct and are kissing loop (KL) complexes.

The term "oligonucleotide" as used herein includes linear oligomers of nucleotides or analogs thereof, including deoxyribonucleosides, ribonucleosides, and the like. Typically, oligonucleotides range in size from a few monomeric units, e.g., 3-4, to several hundreds of monomeric units. Olgionucleotides can have inhibitory activity or stimulatory activity.

As used here, the phrase "5' or 3' sticky ends" is meant to refer to the 3' and/or 5' protruding ends of DNA or RNA that will bond with complementary sequences of bases. In certain embodiments, the RNA motifs have 5' or 3' sticky ends. In certain embodiments, the 5' or 3' sticky ends are located in the middle of a helix. According to the invention, the 5' and 3' sticky ends can be engineered to be used for self-assembly of the nanorings into an RNA nanotube.

By "agent" is meant any small molecule chemical compound, antibody, nucleic acid molecule, or polypeptide, or fragments thereof.

By "ameliorate" is meant decrease, suppress, attenuate, diminish, arrest, or stabilize the development or progression of a disease.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels."

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected.

By "detectable label" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "disease" is meant any condition or disorder that damages or interferes with the normal function of a cell, tissue, or organ.

By "effective amount" is meant the amount of a required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

The invention provides a number of targets that are useful for the development of highly specific drugs to treat or a disorder characterized by the methods delineated herein. In addition, the methods of the invention provide a facile means to identify therapies that are safe for use in subjects. In addition, the methods of the invention provide a route for analyzing virtually any number of compounds for effects on a disease described herein with high-volume throughput, high sensitivity, and low complexity.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

"Hybridization" means hydrogen bonding, which may be Watson-Crick, Hoogsteen, reversed Hoogsteen hydrogen bonding, or other base pairing structures as described by N. B. Leontis & E. Westhof (RNA, (2001), vol. 7, pages 499-512) between complementary nucleobases. For example, adenine and thymine are complementary nucleobases that pair through the formation of hydrogen bonds.

By "inhibitory nucleic acid" is meant a double-stranded RNA, siRNA, shRNA, or antisense RNA, or a portion thereof, or a mimetic thereof, that when administered to a mammalian cell results in a decrease (e.g., by 10%, 25%, 50%, 75%, or even 90-100%) in the expression of a target gene. Typically, a nucleic acid inhibitor comprises at least a portion of a target nucleic acid molecule, or an ortholog thereof, or comprises at least a portion of the complementary strand of a target nucleic acid molecule. For example, an inhibitory nucleic acid molecule comprises at least a portion of any or all of the nucleic acids delineated herein.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

As used herein, "obtaining" as in "obtaining an agent" includes synthesizing, purchasing, or otherwise acquiring the agent.

"Primer set" means a set of oligonucleotides that may be used, for example, for PCR. A primer set would consist of at least 2, 4, 6, 8, 10, 12, 14, 16, 18, 20, 30, 40, 50, 60, 80, 100, 200, 250, 300, 400, 500, 600, or more primers.

By "reduces" is meant a negative alteration of at least 10%, 25%, 50%, 75%, or 100%.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

By "siRNA" is meant a double stranded RNA. Optimally, an siRNA is 18, 19, 20, 21, 22, 23 or 24 nucleotides in length and has a 2 base overhang at its 3' end. These dsRNAs can be introduced to an individual cell or to a whole animal; for example, they may be introduced systemically via the bloodstream. Such siRNAs are used to downregulate mRNA levels or promoter activity.

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "subject" is meant a mammal, including, but not limited to, a human or non-human mammal, such as a bovine, equine, canine, ovine, or feline.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," "treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

(FIG. 2A) The use of RNA NP functionalized at 3'-side with sense strand is limited by 3 specified nts at the seed region of antisense (left scheme). The use of RNA NP functionalized with antisense (right scheme) can minimize this limitation, since the seed region of siRNA is not affected. (FIG. 2B) The use of RNA NP functionalized at 5'-side with antisense strand (right scheme) is limited by 3 specified nts at siRNA seed region. This can be avoided if the RNA NP are functionalized with sense-strand (left scheme). (FIG. 2C) The addition of chemically synthesized sense or antisense strands during the co-transcriptional assembly of 3'-end functionalized RNA NP places no sequence constraints on the design. The solid phase synthesis of 25-nt RNA is relatively simple and inexpensive.

(FIG. 3A) Native-PAGE results representing co-transcriptional body-labeled assemblies leading to the formations of ring RNA NP 5'- or 3'-end functionalized with different numbers of siRNAs (0-6) and dynamic light scattering (DLS) result for assembly. (FIG. 3B) Membrane filtration and (FIG. 3C) native-PAGE purification of co-transcriptionally assembled functional RNA NP. (FIG. 3D) Presence of $Mn^{2+}$ stimulates transcription with regular and chemically modified NTP substrates. The relative amounts of single-stranded RNAs produced in the presence of regular NTPs (blue trace) and ATP, CTP, GTP and 2'-F-dUTP (red trace) are normalized to the standard yields of the non-modified full-length transcript produced in the absence of $MnCl_2$ (conventional transcription buffer). The error bars show standard error from nine independent experiments. (FIG. 3E) native-PAGE results illustrating the formation of co-transcriptionally assembled chemically modified (2'-F-dUTPs) functionalized ring RNA NP. Please note that conventional and 2'-Fl-dUMP-containing nanorings are produced with similar yields.

(FIG. 4A) native-PAGE results representing co-transcriptional assemblies leading to the formation of cube RNA NP 5'- and 3'-end functionalized with different numbers of siRNAs (0-6) and dynamic light scattering (DLS) result for RNA NP assembly. (FIG. 4B) native-PAGE purification of co-transcriptionally assembled functional RNA NP.

(FIG. 6A) Schematic representation of nanocubes and nanorings having all uracils fluorinated. (FIG. 6B) Effect of $MnCl_2$ concentration on the transcription yield of chemically modified (2'-F-dUTP) RNA molecules. Note that at 0.5 mM $MnCl_2$ the yield of chemically modified RNA is similar to the yield of non-modified RNAs in the absence of $MnCl_2$. Presence of $Mn^{2+}$ promotes transcription initiation and extension of the 2'-F-dUMP. Lower bands represent abortive initiation products. (FIGS. 6C & 6D) Native-PAGE and quantification results representing the relative stabilities of chemically modified with 2'-F-dUTPs and non-modified (FIG. 6C) cubes and (FIG. 6D) rings in human blood serum. The time of incubation with 5% human blood serum is shown on top of each gel. Please note that non-modified NP degrade with $t_{1/2}$~12 and ~28 min for cubes and rings respectively, while chemically modified with 2'-F-dUTPs NP stay intact for over ~4 hours.

FIG. 11 discloses SEQ ID NO: 44.

DETAILED DESCRIPTION OF THE INVENTION

Figure 1:
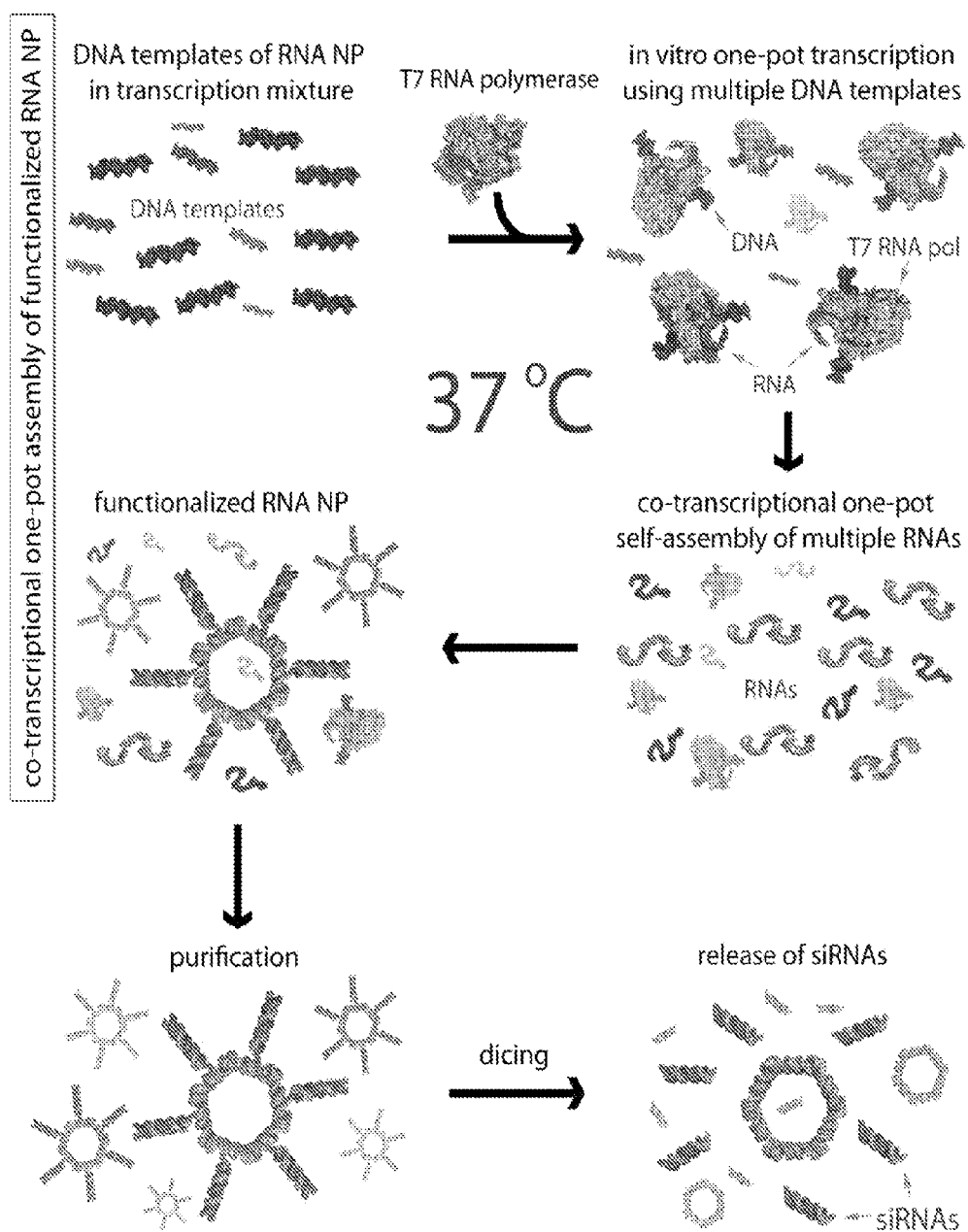
FIG. 1 illustrates the co-transcriptional assemblies of RNA nanoparticles (NP). Schematic representation of co-transcriptional assemblies leading to the formation of RNA NP (nanoring) functionalized with six siRNAs and their further purification. Functional siRNAs can be released by Dicer nuclease.

The invention features compositions and methods that are useful for the one-pot production of chemically modified functional RNA nanoparticles during in vitro transcription with T7 RNA polymerase. The efficiency of incorporation of 2'-fluoro-dNTP in the transcripts by the wild type T7 RNA polymerase dramatically increases in the presence of manganese ions, resulting in a high-yield production of chemically modified RNA nanoparticles functionalized with siRNAs that are resistant to nucleases from human blood serum. Moreover, the unpurified transcription mixture can be used for functional ex vivo pilot experiments.

High yields of RNA NP were generated by eliminating the purification step of individual RNA strands and post-transcriptional assembly of RNA NPs. The claimed methodology is based on in vitro transcription by wild type (wt) T7 RNA polymerase of a mixture of DNA templates encoding RNA strands that go into the composition of the given RNA NP. One embodiment of the claimed method is co-transcriptional assemblies of NPs functionalized at either their 5'- or 3'-ends with siRNAs (0-6 siRNAs per RNA NP). When all 6 siRNAs were present, the NPs were composed of 12 RNA strands each. However, larger complexes may be co-transcriptionally produced as well, e.g. RNA NP composed of any number of RNA strands.

In certain embodiments of the invention two types of RNA NP, nanorings and nanocubes, designed based on intra-molecular and inter-molecular hydrogen bond formation, respectively, are produced by the claimed co-transcriptional assembly method. The RNA NP functionalized at either the 5'- or 3'-side with siRNA duplexes targeting enhanced green fluorescence protein (eGFP) (Afonin, K. A. et al., *Nature protocols* 2011, 6, (12), 2022-34; and Gopalakrishna, S. et al., *Rna* 2004, 10, (11), 1820-30) efficiently silence its expression when transfected into the cultured cells. Formation of RNA NP carrying functional siRNAs in physiological conditions suggests the possibility of their expression in vivo combining gene therapy and RNA nanotechnology approaches.

The invention utilizes wild-type T7 RNA polymerase in a manganese ion containing buffer to produce RNA strands containing modified nucleotides. The RNA strands assemble into RNA nanoparticles co-transcriptionally. T7 RNA polymerase is an RNA polymerase from the T7 bacteriophage that catalyzes the formation of RNA in the 5' to 3' direction from a dsDNA template. T7 RNA polymerase is promoter-specific and transcribes only DNA downstream of the T7 promoter. The polymerase requires a DNA template a magnesium ions as a cofactor for the synthesis of RNA. Applicants discovered that in the presence of low concentrations manganese ions, less than 1 mM, preferably between 0.25 mM and 0.75 mM, and more preferably around 0.5 mM, T7 RNA polymerase incorporates modified nucleotides into the nacsent RNA strand. dsDNA templates can be produced by any means known to those of skill in the art. For example, two or more complementary single stranded DNA templates could be synthesized and annealed to form a defined dsDNA template of predetermined sequence. In another method, oligonucleotide primers could be synthesized and used to amplify a dsDNA template using the polymerase chain reaction. In other embodiments, a target sequence could be ligated into a plasmid adjacent to a T7 promoter within the plasmid. The plasmid could then be linearized by digestion with an endonuclease and the linearized plasmid used as a template for RNA synthesis.

RNA and Nanostructure Design

RNA has a number of advantages for nanostructure design. Nanoparticle structures provide a size range that is large enough to avoid the problem of expulsion from the cell, but are small enough to avoid the problems of cell delivery often encountered with larger particles. RNA is the only biopolymer that can carry genetic information and has catalytic properties. RNA can naturally fold into complex motifs, and RNA motifs are capable of self-assembly. RNA has a natural functionality, for instance RNA can function as ribozymes or riboswitches. Further, RNA is advantageous in eliciting a very low immune response. Moreover, the construction of RNA into ordered, patterned superstuctures has a number of desirable characteristics, including the ability to self-assemble in precisely defined ways, the ability to undergo editing and replication, the ability to undergo controlled disassembly. RNA has versatility in function and structure. Functionally, RNA is the only biopolymer that can carry genetic information and that possesses catalytic properties. Structurally, RNA has predictable intra and intermolecular interactions with well-known structural geometry. The RNA strands that consist of adenine (A), guanine (G), cytosine (C), and uridine (U) can naturally, or can be programmed, to self-assemble via complementary base pairing. The helical region of RNA has a well-known nanometer scale structural geometry of 2.86 nm per helical turn with 11 base pairs and a 2.3 nm diameter. The self-assembly of RNA into complex structures can be facilitated via complementary base pairing or inter- and intra-molecular interactions of the different single stranded regions in the RNA, including internal bulges and loop motifs, and single-stranded overhangs or "sticky-ends".

The methods of the invention can be used to assemble RNA NPs composed of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 112, 113, 114, 115, 116, 117, 118, 119, 120, 121, 122, 123, 124, 125 or more distinct RNA strands RNA Self-Assembly Small RNA structural motifs can code the precise topology of large molecular architectures. It has been shown that RNA structural motifs participate in a predictable manner to stabilize, position and pack RNA helices without the need of proteins (Chworos A et al., Science 306:2068-2072.2004). RNAI and RNAII are loop structures that interact in what is called a 'kiss' or 'kissing' complex (Lee et al., Structure 6:993-1005.1998). This contact facilitates the pairing of the RNAI and RNAII loops, until the two RNAs form a duplex. As such, the "kissing" interaction between RNAI and RNAII is one means of self-assembly between the RNA building blocks. The interaction between the RNAIi/RNAIIi complex involves all the bases in the base pairing, and dissociates nearly 7000 times more slowly than the wild-type complex.

The self-assembly of nanoparticles from RNA involves cooperative interaction of individual RNA molecules that spontaneously assemble in a predefined manner to form a larger two- or three-dimensional structure. Within the realm of self-assembly two main categories have been described: template and non-template (Lee et al. J Nanosci Nanotechnol. 2005 December; 5(12):1964-82). Template assembly involves interaction of RNA molecules under the influence of specific external sequence, forces, or spatial constraints such as RNA transcription, hybridization, replication, annealing, molding, or replicas. In contrast, non-template assembly involves formation of a larger structure by individual components without the influence of external forces. Examples of non-template assembly are ligation, chemical conjugation, covalent linkage, and loop/loop interaction of RNA, especially the formation of RNA multimeric complexes (Lee et al. 2005, as above).

Previously, RNA has been demonstrated to assemble into nanoparticles of various shapes and sizes. The first RNA nanoparticles were generated using loop-receptor interfaces to form dimeric nanoparticles. The assembly of this H-shaped nanoparticle was mediated by GAAA/Hnt receptor interaction, which is a highly recurrent motif found in group I and group II introns and other ribozymes and riboswitches. This interaction was further used to generate oriented filaments by combining multiple loop-receptor interactions with a four-way junction motif. One of the first examples of RNA nanoparticles that incorporate multiple RNA motifs within its context is the tectosquare, which is composed of four artificial RNA building blocks called tectoRNAs that self-assemble through specific, non-covalent loop-loop interactions called kissing loops (KL) found at the end of each stem. These tectoRNAs were further programmed to self-assemble into complex arrays via 3' sticky tails with controllable topology, directionality and geometry. The first example of a therapeutic RNA nanoparticle was designed from phi-29-encoded packaging motor (pRNA), a natural RNA motif found in bacteriophages. The pRNA dimers were reengineered for targeted delivery of ribozymes to attack the hepatitis B virus by specifically cleaving the virus's poly-A signal. In a subsequent study, the pRNA trimers were functionalized with cell receptor-binding RNA aptamers and were used to deliver siRNAs that target a specific gene for silencing and thus enabling apoptosis in cancer cells.

In certain embodiments the RNA building blocks of the invention can self-assemble in buffer conditions suitable for RNA, and that can be determined by one of skill in the art. In preferred embodiments the RNA strands assemble into RNA NPs co-transcriptionally. dsDNA templates are provided and mixed with wild type T7 RNA polymerase in a buffer containing manganese ions and at least one modified nucleotide. In certain embodiments the manganese ion is present at concentrations of less than 1 mM. In other embodiments, the manganese ion concentration is in a range from 0.25 mM to 0.75 mM. In preferred embodiments the manganese ions are present at 0.5 mM.

RNA Nanoparticles

RNA has been demonstrated to be an efficient nanoparticle. A bacteriophage phi29-encoded RNA (pRNA) has been reengineered to form dimmers, trimers, rods, hexamers, and 3D arrays several microns in size through interactions of interlocking loops (Shu, D.; Moll, W.-D.; Deng, Z.; Mao, C.; Guo, P. Nano Letters 2004, 4, (9), 1717-1723; Guo, P. J Nanosci Nanotechnol 2005, 5, (12), 1964-82). A nanoparticle, containing a pRNA trimer as a delivery vehicle was used to deliver siRNAs and receptor-binding aptamers, and has been demonstrated to block cancer development both in vitro in cell culture, and in vivo in mice (Khaled, A.; Guo, S.; Li, F.; Guo, P. Nano Lett 2005, 5, (9), 1797-808; Guo, S.; Huang, F.; Guo, P. Gene Ther 2006, 13, (10), 814-20). An H-shaped RNA molecular unit built from a portion of group I intron domain has been shown to form oriented filaments (Hansma, H. G.; Oroudjev, E.; Baudrey, S.; Jaeger, L. J Microsc 2003, 212, (Pt 3), 273-9; Nasalean, L.; Baudrey, S.; Leontis, N. B.; Jaeger, L. Nucleic Acids Res 2006, 34, (5), 1381-92). Further, specific RNA nano-arrangements based on HIV dimerization initiation site stem-loops were shown to be capable of thermal isomerization to alternative structures (Horiya, S.; Li, X.; Kawai, G.; Saito, R.; Katoh, A.; Kobayashi, K.; Harada, K. Nucleic Acids Res Suppl 2002, (2), 41-2; Horiya, S.; Li, X.; Kawai, G.; Saito, R.; Katoh, A.; Kobayashi, K.; Harada, K. Chem Biol 2003, 10, (7), 645-54.; Li, X.; Horiya, S.; Harada, K. J Am Chem Soc 2006, 128, (12), 4035-40). Small structural fragments found in the ribosome and HIV have been used in the design of artificial RNA building blocks, called tectoRNAs (Chworos, A.; Severcan, I.; Koyfman, A. Y.; Weinkam, P.; Oroudjev, E.; Hansma, H. G.; Jaeger, L. Science 2004, 306, (5704), 2068-72). Each tectoRNA contains a right angle motif that forms a 90-degree angle between adjacent helices, two interacting hairpin loops at the end of each stem, and a 3' "sticky stem". The hairpin loops direct the formation of the tetramer via formation of specific noncovalent loop-loop interactions, called "kissing loops", and the "sticky stems" further assemble tetramers into complex nanoarrays. In bionanotechnology, RNA-RNA interactions can guide precise deposition of gold nanoparticles (Bates, A. D.; Callen, B. P.; Cooper, J. M.; Cosstick, R.; Geary, C.; Glidle, A.; Jaeger, L.; Pearson, J. L.; Proupin-Perez, M.; Xu, C.; Cumming, D. R. Nano Lett 2006, 6, (3), 445-8). For example, self-assembling tectoRNA-ladders have been shown to induce a precise linear arrangement of cationic gold nanoparticles, demonstrating that RNA can control regular spacing of gold nanoparticles and can act as a nanocrown scaffold (Koyfman, A. Y.; Braun, G.; Magonov, S.; Chworos, A.; Reich, N. O.; Jaeger, L. J Am Chem Soc 2005, 127, (34), 11886-7).

Design

The general approach used to create RNA nano-particles and nano-materials is to take known RNA structures, cut them into the building blocks, and reengineer single-stranded loops and regions to facilitate the desired self-assembly. The self-assembly of all the above discussed RNA building blocks into nanostructures is mediated by the complementarity of hairpin loops and loop receptors that form non-covalent RNA-RNA interactions. For precise assembly of the RNA building blocks, each of the corresponding complementary loop-loop interactions are uniquely reengineered.

The instant invention describes polyvalent RNA nanoparticles containing modified nucleotides that comprise RNA motifs as building blocks which are assembled co-transcriptionally. In certain embodiments, the building blocks comprise a motif that allows for non-covalent co-transcriptional assembly between 2 or more building blocks.

A number of RNA motifs are available as building blocks, including but not limited to RNA I and/or RNA II motifs, kissing loops, RNA I inverse (RNA Ii) and/or RNA II inverse (RNA IIi) motifs. Numerous high-resolution RNA structures determined by NMR or X-ray crystallography can be separated into building blocks for design of new RNA nanoparticles and nanomaterials.

In certain embodiments of the invention, the RNAII motif is a 90 degree angle bend motif. In certain preferred embodiments, these motifs, embedded within rationally designed RNAs (tectoRNA), are chosen in order to generate square-shaped tetrameric RNA nanoparticles (NPs).

In further preferred embodiments, the RNAII motif is selected from the group consisting of right angle (RA) motifs, three way junction (3WJ) motifs, four way junction motifs and class II tRNA motifs.

In further preferred embodiments, the RA-motif can form at least 10 tertiary H-bonds and 4 stacking interactions, the 3WJ-niotif at least 14 H-bonds and 9 stacks, while the tRNA motif can form approximately 33 H-bonds and 15 stacking interactions.

Preferably, the three different 90° motifs can be used as structural cores for designing L-shaped tectoRNAs able to assemble into tectosquares.

The polyvalent RNA nanoparticle of according to the invention can be in the shape of a ring, in the shape of a square or in the shape of a triangle; however it is to be understood that other geometries are possible. Accordingly, the ring, square, triangle or other shape comprises 1, 2, 3, 4, 5, 6, 7, 8, 9, 10, 11, 12, 13, 14, 15, 16, 17, 18, 19, 20, 21, 22 or more building blocks as described by the invention. In certain preferred embodiments of the invention, the ring comprises 6 building blocks that form a hexameric ring. In the hexameric ring, there is a 120-degree angle at the loop-loop interactions at the corners of the hexameric ring.

In the tectosquares, there in a 90-degree angle at the loop-loop interactions at the corners of the squares.

In certain embodiments, there is a positive relationship between the stability of RNA assemblies and the complexity of the tertiary structures that define the assembly.

The RNA building blocks can contain hairpin loops. In certain specific example, each building block contains two or more hairpin loops. The hairpin loops are connected by a helix. The RNA building blocks can be held together by non-covalent loop-loop contacts. Further, the building blocks have 5' or 3' sticky ends, and in certain preferred embodiments of the invention, the 5' or 3' sticky ends are located in the middle of a helix.

As described, the polyvalent RNA nanoparticles consist of building blocks, which have 5' or 3' sticky ends. These 5' or 3' sticky ends can be engineered as sticky ends for self-assembly into polyhedral architecture. Advantageously, in certain embodiments, the RNA nanoparticles can be connected via complementary ends. This polyvalent RNA nanoparticle is capable of self-assembly. As discussed herein, in certain preferred embodiments, self-assembly may occur as a single-step process.

The enzyme RNase H is a non-specific endonuclease and catalyzes the cleavage of RNA via a hydrolytic mechanism. Members of the RNase H family can be found in nearly all organisms, from archaea to bacteria and eukaryota. RNase H's ribonuclease activity cleaves the 3'-O—P bond of RNA in a DNA/RNA duplex to produce 3'-hydroxyl and 5'-phosphate terminated products. In DNA replication, RNase H is responsible for removing the RNA primer, allowing completion of the newly synthesized DNA. In a molecular biology laboratory, as RNase H specifically degrades the RNA in RNA:DNA hybrids and will not degrade DNA or unhybridized RNA, it is commonly used to destroy the RNA template after first-strand complementary DNA (cDNA) synthesis by reverse transcription, as well as procedures such as nuclease protection assays. RNase H can also be used to degrade specific RNA strands when the cDNA oligo is hybridized, such as the removal of the poly(A) tail from mRNA hybridized to oligo(dT), or the destruction of a chosen non-coding RNA inside or outside the living cell.

In certain embodiments of the present invention, the method further comprises adding RNase H. While 5' extension of the RNA strands dramatically increases the yield of the full-length product, it is also expected to interfere with the nanocube assembly. To resolve this problem and remove the extra RNA from the 5' end of the nanocube strand, 13-nt oligodeoxynucleotides complementary to the 5' end of the extended transcriptcan be added and the resulting heteroduplex can be treated with ribonuclease H. This treatment results in the removal of the 5' extension.

RNA Nanotubes

As described, the polyvalent RNA nanoparticles consist of building blocks, which have 5' or 3' sticky ends. These 5' or 3' sticky ends can be engineered as sticky ends for self-assembly of nanorings into an RNA nanotube. Advantageously, in certain embodiments, the RNA nanoparticles can be connected via complementary ends. This polyvalent RNA nanoparticle is capable of self-assembly into a nanotube. As discussed herein, in certain preferred embodiments, self-assembly may occur as a single-step process.

Conjugation to Nanoparticles

The polyvalent RNA nanoparticles can be used to deliver therapeutics, as diagnostic tools, or as delivery agents. Advantageously, the 5' and 3' sticky ends are positions for conjugation of one or more therapeutic, diagnostic, or delivery agents.

Exemplary potential applications of multi-functional nanoparticles of the invention in which 2, 3, 4, or more agents are coupled to a nanoparticle include using one or more agents to target a macromolecular structure or a cell and using the second one to alter the function/properties of the macromolecule or cell, e.g., using a protein to target a cell and using a toxin or cell death protein to kill the targeted cell, using an siRNA to silence genes, or using a fluorescent particle for visualization, or using a chemical or protein to target a protein within a complex and another one to alter the function of a different component of the complex.

Further exemplary potential applications of the multi-functional nanoparticles of the invention include use of the nanoparticles as riboswitch aptamers, ribozymes, or beacons.

Riboswitches are a type of control element that use untranslated sequence in an mRNA to form a binding pocket for a metabolite that regulates expression of that gene. Riboswitches are dual function molecules that undergo conformational changes and that communicate metabolite binding typically as either increased transcription termination or reduced translation efficiency via an expression platform.

Ribozymes catalyze fundamental biological processes, such as RNA cleavage by transesterification. The polyvalent RNA nanoparticles of the invention can be incorporated in to ribozymes using methods described in, for example, U.S. Pat. No. 6,916,653, incorporated by reference in its entirety herein.

A number of "molecular beacons" (often fluorescence compounds) can be attached to RNA nanoparticles of the invention to provide a means for signaling the presence of, and quantifying, a target analyte. Molecular beacons, for example, employ fluorescence resonance energy transfer-based methods to provide fluorescence signals in the presence of a particular analyte/biomarker of interest. In preferred embodiments, the term "molecular beacon" refers to a molecule or group of molecules (i.e., a nucleic acid molecule hybridized to an energy transfer complex or chromophore(s)) that can become detectable and can be attached to a nanoparticle under preselected conditions. Similarly, amplifying fluorescent polymers (AFPs) can be utilized in the present invention. An AFP is a polymer containing several chromophores that are linked together. As opposed to isolated chromophores that require 1:1 interaction with an analyte in conventional fluorescence detection, the fluorescence of many chromophores in an AFP can be influenced by a single molecule. For example, a single binding event to an AFP can quench the fluorescence of many polymer repeat units, resulting in an amplification of the quenching. Quenching is a process which decreases the intensity of the fluorescence emission. Molecular beacons and AFPs, including their methods for preparation, that can be used in the present invention are described in numerous patents and publications, including U.S. Pat. No. 6,261,783.

Any protein can be coupled to nanoparticles. For instance, glycoproteins are most easily coupled, as they can be oxidized to generate an active aldehyde group. Other proteins can be coupled via their —COOH group(s) but with lower efficiency. However, other means known in the art, such as di-imide reagents, e.g. carbodiimide can be used to couple proteins lacking sugars to the nanoparticles.

Polyethylene glycol (PEG) chains can be conjugated to the nanoparticles. PEG chains render the nanotubes highly water-soluble. PEG-phospholipids (PEG-PL) have been used in the formation of micelles and liposomes for drug delivery (Adlakha-Hutcheon, G.; Bally, M. B.; Shew, C. R.; Madden, T. D. Nature Biotech. 1999, 17, 775-779; Meyer, O.; Kirpotin, D.; Hong, K.; Sternberg, B.; Park, J. W.; Woodle, M. C.; Papahadjopoulos, D. J. Biol. Chem. 1998, 273, 15621-15627; Papahadjopoulos, D.; Allen, T. M.; Gabizon, A.; Mayhew, E.; Matthay, K.; Huang, S. K.; Lee, K. D.; Woodle, M. C.; Lasic, D. D.; Redemann, C.; Martin, F. J. Proc. Nat. Acad. Sci. USA. 1991, 88, 11460-11464).

Functional groups can be coupled to the nanoparticle, for instance the functional group can be a reactive functional group. Suitable functional groups include, but are not limited to, a haloacetyl group, an amine, a thiol, a phosphate, a carboxylate, a hydrazine, a hydrazide an aldehyde or a combination thereof. Other functional groups include groups such as a reactive functionality or a complementary group. In addition, RNA functional groups can be attached, as for example ribozymes or riboswitch aptamers.

The nanoparticle can be used for attachment of small molecules for specific interactions with nucleic acids, carbohydrates, lipids, proteins, antibodies, or other ligands.

The nanoparticle can have dyes attached. The dye is can be a fluorescent dye, or a plurality of fluorescent dyes. Suitable dyes include, but are not limited to, YOYO-1, JOJO-1, LOLO-1, YOYO-3, TOTO, BOBO-3, SYBR, SYTO, SYTOX, PicoGreen, OliGreen, and combinations thereof. Other dyes include, thiazole orange, oxazole yellow, or non-intercalating dyes such as fluorescein, rhodamine, cyanine or coumarin based dyes, and combinations thereof. Other suitable dyes include, but are not limited to, 4-acetamido-4'-isothiocyanatostilbene-2,2'disulfonic acid; acridine and derivatives: acridine, acridine isothiocyanate; 5-(2'-aminoethyl)aminonap-hthalene-1-sulfonic acid (EDANS); 4-amino-N-[3-vinylsulfonyl)phenyl]naphth-alimide-3,5 disulfonate; N-(4-anilino-1-naphthyl)maleimide; anthranilamide; BODIPY; Brilliant Yellow; coumarin and derivatives: coumarin, 7-amino-4-methylcoumarin (AMC, Coumarin 120), 7-amino-4-trifluoromethylcouluarin (Coumaran 151); cyanine dyes; cyanosine; 4',6-diaminidino-2-phenylindole (DAPI); 5',5''-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,-2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives: erythrosin B, erythrosin, isothiocyanate; ethidium; fluorescein and derivatives: 5-carboxyfluorescein (FAM), 5-(4,6-dichlorotriazin-2-yl)aminofluorescein (DTAF), 2',7'-dimethoxy-4'5'-dichloro-6-carboxyfluorescein (JOE), fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid; terbium chelate derivatives; Cy 3; Cy 5; Cy 5.5; Cy 7; IRD 700; IRD 800; La Jolla Blue; phthalocyanine; and naphthalo cyanine. Suitable dyes for use in the nanoparticles of the present invention include, without limitation, a family of homodimeric cyanine DNA intercalating dyes from Molecular Probes that cover the visible spectrum, such as YOYO-1 (488/509), JOJO-1 (532/545), LOLO-1 (565/579), and YOYO-3 (612/631), SYBR-101 (488/505) and SYTO-62 (652/676). Given sufficient detection SN, dyes are mixed in various ratios in a single particle such that, for example, different fluorescence spectra are obtained from mixtures of just 2 dyes.

According to the invention, one or more therapeutic, diagnostic, or delivery agents are directly included in the building block sequences. In certain embodiments, the delivery agent can be a targeting agent. Targeting agents are used to direct the nanoparticle to a tissue or cell target. An exemplary embodiment of a targeting agent is an antibody. For example, antibodies suitable for use as targeting agents in the present invention include antibodies directed to cell surface antigens which cause the antibody-nanoparticle complex to be internalized, either directly or indirectly. For example, in the treatment of cancer, suitable antibodies include antibodies to CD33 and CD22. CD33 and CD22 that are over-expressed and dimerized on lymphomas.

A therapeutic agent can be coupled to the nanoparticle for prevention or treatment of a disease or condition. The therapeutic agent is selected from, but not limited to: siRNA, aptamers, oligonucleotides, antisense RNA, chemotherapeutic agents, ribozymes, and, fluorescent beads, heavy metals, radioisotopes, quantum dots, and molecular beacons.

A delivery agent can be coupled to the nanoparticle. The delivery agent is selected from, but not limited to: liposomes, antibodies, polyamines, polyethylene glycol. In addition, the delivery vehicle may be the naked RNA particle itself.

A wide variety of particles sizes are suitable for the present invention. In certain aspects, the particle has a diameter of about 10 nanometers to about 10 microns. Preferably the particle diameter is about 10 to 700 nanometers, and more preferably, the diameter of about 10 nanometers to about 100 nanometers.

The polyvalent RNA nanoparticle or the polyvalent RNA nanotube as described herein has a number of uses. For example, the polyvalent RNA nanoparticle or the polyvalent RNA nanotube can be used in drug delivery, imaging, nanocircuits, cell growth surfaces, medical implants, medical testing, or gene therapy.

In one particular embodiment, the polyvalent RNA nanoparticle or the polyvalent RNA nanotube as described can be used in biological meshes. In one exemplary embodiment, the invention as described herein may find use as a biosensor in, for example, pathogen detection. In one particular embodiment, self-assembling nano-meshes are used to attach biosensors for pathogen detection or for x-ray crystallography by placing multiple copies of a protein or functional RNAs, for example, on the mesh. Biosensors for pathogen detection are advantageously employed in bioterrorism capacities.

In another exemplary embodiment, nanotubes of the invention, as described herein, are employed as skeletons or scaffolds for tissue growth.

These uses are exemplary, and not considered to be limiting.

Compositions

The invention, in part, pertains to a drug delivery composition comprising the polyvalent RNA nanoparticle as described herein. The drug delivery composition of the invention can gain entry into a cell or tissue.

Advantageously, the drug delivery composition of the invention provides for a more controlled delivery of an active agent, especially a therapeutic agent, to a site of action at an optimum rate and therapeutic dose. Thus, improvements in therapeutic index may be obtained by modulating the distribution of the active ingredient in the body. Association of the active ingredient with a delivery system enables, in particular, its specific delivery to the site of action or its controlled release after targeting the action site. By reducing the amount of active ingredient in the compartments in which its presence is not desired, it is possible to increase the efficacy of the active ingredient, to reduce its toxic side effects and even modify or restore its activity.

It is understood by one of skill in the art that changing the base composition of RNA changes the half-life of RNA and thus the release of RNA from the composition. For instance, the composition can be modified to consist of fast release, slow release or a staged release of polyvalent RNA nanoparticle.

In certain preferred embodiments, the drug delivery composition can comprise a second therapeutic agent. In some embodiments, the composition comprising nanoparticles and the second therapeutic agent are administered simultaneously, either in the same composition or in separate compositions. In some embodiments, the nanoparticle composition and the second therapeutic agent are administered sequentially, i.e., the nanoparticle composition is administered either prior to or after the administration of the second therapeutic agent. The term "sequential administration" as used herein means that the drug in the nanoparticle composition and the second agent are administered with a time separation of more than about 15 minutes, such as more than about any of 20, 30, 40, 50, 60 or more minutes. Either the nanoparticle composition or the chemotherapeutic agent may be administered first. The nanoparticle composition and the chemotherapeutic agent are contained in separate compositions, which may be contained in the same or different packages. In some embodiments, the administration of the nanoparticle composition and the second therapeutic agent are concurrent, i.e., the administration period of the nanoparticle composition and that of the second therapeutic agent overlap with each other. In some embodiments, the administration of the nanoparticle composition and the second therapeutic agent are non-concurrent. For example, in some embodiments, the administration of the nanoparticle composition is terminated before the second therapeutic agent is administered. In some embodiments, the administration of the second therapeutic agent is terminated before the nanoparticle composition is administered. Administration may also be controlled by designing the RNA nanoparticle or nano-tube to have different half lives. Thus, particle dissolution would be controlled by a timed release based upon variations in designed RNA stability.

The second therapeutic agent is selected from, but not limited to chemotherapeutic agents, cardiovascular drugs, respiratory drugs, sympathomimetic drugs, cholinomimetic drugs, adrenergic or adrenergic neuron blocking drugs, analgesics/antipyretics, anesthetics, antiasthmatics, antibiotics, antidepressants, antidiabetics, antifungals, antihypertensives, anti-inflammatories, antianxiety agents, immunosuppressive agents, immunomodulatory agents, antimigraine agents, sedatives/hypnotics, antianginal agents, antipsychotics, antimanic agents, antiarrhythmics, antiarthritic agents, antigout agents, anticoagulants, thrombolytic agents, antifibrinolytic agents, hemorheologic agents, antiplatelet agents, anticonvulsants, antiparkinson agents, antihistamines/antipruritics, agents useful for calcium regulation, antibacterials, antivirals, antimicrobials, anti-infectives, bronchodilators, hormones, hypoglycemic agents, hypolipidemic agents, proteins, peptides, nucleic acids, agents useful for erythropoiesis stimulation, antiulcer/antireflux agents, antinauseants/antiemetics and oil-soluble vitamins, or combinations thereof.

When the second therapeutic agent is a chemotherapeutic agent, the chemotherapeutic agent is selected from, but not limited to, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine, mechlorethamine oxide hydrochloride rethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, improsulfan, benzodepa, carboquone, triethylenemelamine, triethylenephosphoramide, triethylenethiophosphoramide, trimethylolomelamine, chlornaphazine, novembichin, phenesterine, trofosfamide, estermustine, chlorozotocin, gemzar, nimustine, ranimustine, dacarbazine, mannomustine, mitobronitol, aclacinomycins, actinomycin F(1), azaserine, bleomycin, carubicin, carzinophilin, chromomycin, daunorubicin, daunomycin, 6-diazo-5-oxo-1-norleucine, doxorubicin, olivomycin, plicamycin, porfiromycin, puromycin, tubercidin, zorubicin, denopterin, pteropterin, 6-mercaptopurine, ancitabine, 6-azauridine, carmofur, cytarabine, dideoxyuridine, enocitabine, pulmozyme, aceglatone, aldophosphamide glycoside, bestrabucil, defofamide, demecolcine, elfornithine, elliptinium acetate, etoglucid, flutamide, hydroxyurea, lentinan, phenamet, podophyllinic acid, 2-ethylhydrazide, razoxane, spirogermanium, tamoxifen, taxotere, tenuazonic acid, triaziquone, 2,2',2"-trichlorotriethylamine, urethan, vinblastine, vincristine, vindesine and related agents. 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; betaalethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cisporphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; taxel; taxel analogues; taxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine;

romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. Preferred additional anti-cancer drugs are 5-fluorouracil and leucovorin. Additional cancer therapeutics include monoclonal antibodies such as rituximab, trastuzumab and cetuximab.

Reference to a chemotherapeutic agent herein applies to the chemotherapeutic agent or its derivatives and accordingly the invention contemplates and includes either of these embodiments (agent; agent or derivative(s)). "Derivatives" or "analogs" of a chemotherapeutic agent or other chemical moiety include, but are not limited to, compounds that are structurally similar to the chemotherapeutic agent or moiety or are in the same general chemical class as the chemotherapeutic agent or moiety. In some embodiments, the derivative or analog of the chemotherapeutic agent or moiety retains similar chemical and/or physical property (including, for example, functionality) of the chemotherapeutic agent or moiety.

The invention also relates to pharmaceutical or diagnostic compositions comprising the nanoparticles of the invention and a pharmaceutically acceptable carrier. The phrase "pharmaceutically acceptable carrier" is art recognized and includes a pharmaceutically acceptable material, composition or vehicle, suitable for administering compounds used in the methods described herein to subjects, e.g., mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Suitable pharmaceutical carriers are described in Remington's Pharmaceutical Sciences, Mack Publishing Company, a standard reference text in this field.

Modified RNA Nanoparticles

The invention encompasses methods of producing stabilized RNA NPs having modifications that protect against 3' and 5' exonucleases as well as endonucleases. Such modifications desirably maintain target affinity while increasing stability in vivo. In various embodiments, the invention includes methods of producing RNA NPs having chemical substitutions at the ribose and/or phosphate and/or base positions of a given nucleobase sequence. Modified nucleotides are incorporated into the nascent RNA strands during transcription in the presence of 0.25 to 0.75 mM $Mn^{2+}$. For example, the invention provides for methods of producing RNA NPs that include chemical modifications at the 2' position of the ribose moiety, circularization of the aptamer, 3' capping and 'spiegelmer' technology. RNA NPs having A and G nucleotides sequentially replaced with their 2'-OCH3 modified counterparts are particularly useful in the methods of the invention. Such modifications are typically well tolerated in terms of retaining affinity and specificity. In various embodiments, RNA NPs produced by the methods of the invention include at least 10%, 25%, 50%, or 75% modified nucleotides. In other embodiments, as many as 80-90% of the RNA NPs' nucleotides contain stabilizing substitutions. In other embodiments, 2'-OMe containing RNA NPs are co-transcriptionally synthesized. Such RNA NPs are desirable because they are inexpensive to synthesize and natural polymerases do not accept 2'-OMe nucleotide triphosphates as substrates so that 2'-OMe nucleotides cannot be recycled into host polynucleotides. Using methods described herein, RNA NPs will be selected for increased in vivo stability. In one embodiment, nuclease resistant RNA NPs having 2'-F and 2'-$OCH_3$ modifications are co-transcriptionally synthesized using T7 RNA polymerase in the presence of $Mn^{2+}$ ions. In other embodiments, the nucleic acids of the invention have one or more locked nucleic acids (LNA). LNA refers to a modified RNA nucleotide. The ribose of the LNA is modified with an extra bridge connecting the 2' oxygen and the 4' carbon which locks the ribose into the North or 3'-endo conformation. See e.g., Kaur, H. et al., *Biochemistry*, vol. 45, pages 7347-55; and Koshkin, A. A., et al., *Tetrahedron*, vol. 54, pages 3607-3630. In other embodiments, one or more nucleic acids of the invention incorporate a morpolino structure where the nucleic acid bases are bound to morpholine rings instead of deoxyribose rings and are linked through phosphorodiamidate groups instead of phosphates. See eg., Summerton, J. and Weller, D., *Antisense & Nucleic Acid Drug Development*, vol. 7, pages 187-195. Yet other modifications, include (PS)-phosphate sulfur modifications wherein the phosphate backbone of the nucleic acid is modified by the substitution of one or more sulfur groups for oxygen groups in the phosphate backbone. Other modifications that stabilize nucleic acids are known in the art and are described, for example, in U.S. Pat. No. 5,580,737; and in U.S. Patent Application Publication Nos. 20050037394, 20040253679, 20040197804, and 20040180360.

In the method of the invention, the modified nucleotide is a monophosphate of $m^1A$ (1-methyladenosine); $m^2A$ (2-methyladenosine); Am (2'-O-methyladenosine); $ms^2 m^6A$ (2-methylthio-$N^6$-methyladenosine); $i^6A$ ($N^6$-isopentenyladenosine); $ms^2i6A$ (2-methylthio-$N^6$ isopentenyladenosine); $io^6A$ ($N^6$-(cis-hydroxyisopentenyl)adenosine); $ms^2i^6A$ (2-methylthio-$N^6$-(cis-hydroxyisopentenyl)adenosine); $g^6A$ ($N^6$-glycinylcarbamoyladenosine); $t^6A$ ($N^6$-threonylcarbamoyladenosine); $ms^2t^6A$ (2-methylthio-$N^6$-threonyl carbamoyladenosine); $m^6t^6A$ ($N^6$-methyl-$N^6$-threonylcarbamoyladenosine); $hn^6A$($N^6$-hydroxynorvalylcarbamoyladenosine); $ms^2hn^6A$ (2-methylthio-$N^6$-hydroxynorvalyl carbamoyladenosine); Ar(p) (2'-O-ribosyladenosine (phosphate)); I (inosine); $m^1I$ (1-methylinosine); $m^1Im$ (1,2'-O-dimethylinosine); $m^3C$ (3-methylcytidine); Cm (2'-O-methylcytidine); $s^2C$ (2-thiocytidine); $ac^4C$(N4-acetylcytidine); $f^5C$ (5-formylcytidine); $m^5$ Cm (5,2'-O-dimethylcytidine); $ac^4Cm$ ($N^4$-acetyl-2'-O-methylcytidine); $k^2C$ (lysidine); m1G (1-methylguanosine); $m^2G$ (N2-methylguanosine); $m^7G$ (7-methylguanosine); Gm (2'-O-methylguanosine); dimethylguanosine); $m^2_2$ G ($N^2,N^2$-dimethylguanosine); $m^2Gm$ ($N^2,2'$-O-dimethylguanosine); $m^2_2$ Gm ($N^2,N^2,2'$-O-trimethylguanosine); Gr(p) (2'-O-ribosylguanosine (phosphate)); yW (wybutosine); $o_2yW$ (peroxywybutosine); OHyW (hydroxywybutosine); OHyW* (undermodified hydroxywybutosine); imG (wyosine); mimG (methylwyosine); Q (queuosine); oQ (epoxyqueuosine); galQ (galactosyl-queuosine); manQ (mannosyl-queuosine); $preQ_0$ (7-cyano-7-deazaguanosine); $preQ_1$ (7-aminomethyl-7-deazaguanosine); $G^+$ (archaeosine); D (dihydrouridine); $m^5Um$ (5,2'-O-dimethyluridine); $s^4U$ (4-thiouridine); $m^5s2U$ (5-methyl-2-thiouridine); $s^2Um$ (2-thio-2'-O-methyluridine); $acp^3U$ (3-(3-amino-3-carboxypropyl)uridine); $ho^5U$ (5-hydroxyuridine); $mo^5U$ (5-methoxyuridine); $cmo^5U$ (uridine 5-oxyacetic acid); $mcmo^5U$ (uridine 5-oxyacetic acid methyl ester); $chm^5U$ (5-(carboxyhydroxymethyl)uridine)); $mchm^5U$ (5-(carboxyhydroxymethyl)uridine methyl ester); $mcm^5U$ (5-methoxycarbonylmethyluridine); $mcm^5Um$ (5-methoxycarbonylmethyl-2'-O-methyluridine); $mcm^5s^2U$ (5-methoxycarbonylmethyl-2-thiouridine); $nm^5s2U$ (5-aminomethyl-2-thiouridine); $mnm^5U$ (5-methylaminomethyluridine); $mnm^5s^2U$ (5-methylaminomethyl-2-thiouridine); $mnm^5se2U$ (5-methylaminomethyl-2-selenouridine); $ncm^5U$ (5-carbamoylmethyluridine); $ncm^5Um$ (5-carbamoylmethyl-2'-O-methyluridine); $cmnm^5U$ (5-carboxymethylaminomethyluridine); $cmnm^5Um$ (5-carboxymethylaminomethyl-2'-O-methyluridine); $cmnm^5$ s2U (5-carboxymethylaminomethyl-2-thiouridine); $m6_2A$ ($N^6$, $N^6$-dimethyladenosine); Im (2'-O-methylinosine); $m^4C$(N4-methylcytidine); $m^4$ Cm ($N^4,2'$-O-dimethylcytidine); $hm^5C$ (5-hydroxymethylcytidine); $m^3U$ (3-methyluridine); $cm^5U$ (5-carboxymethyluridine); $m^6Am$ (N6,2'-O-dimethyladenosine); $m^6_2Am$ ($N^6,N^6$-O-2'-trimethyladenosine); $m^2$ 7G ($N^2,7$-dimethylguanosine); $m^2,2,7G$ ($N^2,N2,7$-trimethylguanosine); $m^3Um$ (3,2'-O-dimethyluridine); $m^5D$ (5-methyldihydrouridine); $f^5Cm$ (5-formyl-2'-O-methylcytidine); $m^1Gm$ (1,2'-O-dimethylguanosine); $m^1Am$ (1,2'-O-dimethyladenosine); $\tau m^5U$ (5-taurinomethyluridine); $\tau m^5s2U$ (5-taurinomethyl-2-thiouridine)); imG-14 (4-demethylwyosine); imG2 (isowyosine); or $ac^6A$ (N6-acetyladenosine).

In preferred embodiments the modified nucleotide is 2'-fluoro-dUMP, 2'-fluoro-dCMP, 2'-fluoro-dGMP, 2'-fluoro-dAMP, or 8-$N_3$AMP.

The following examples are put forth so as to provide those of ordinary skill in the art with a complete disclosure and description of how to make and use the assay, screening, and therapeutic methods of the invention, and are not intended to limit the scope of what the inventors regard as their invention.

Figure 2:
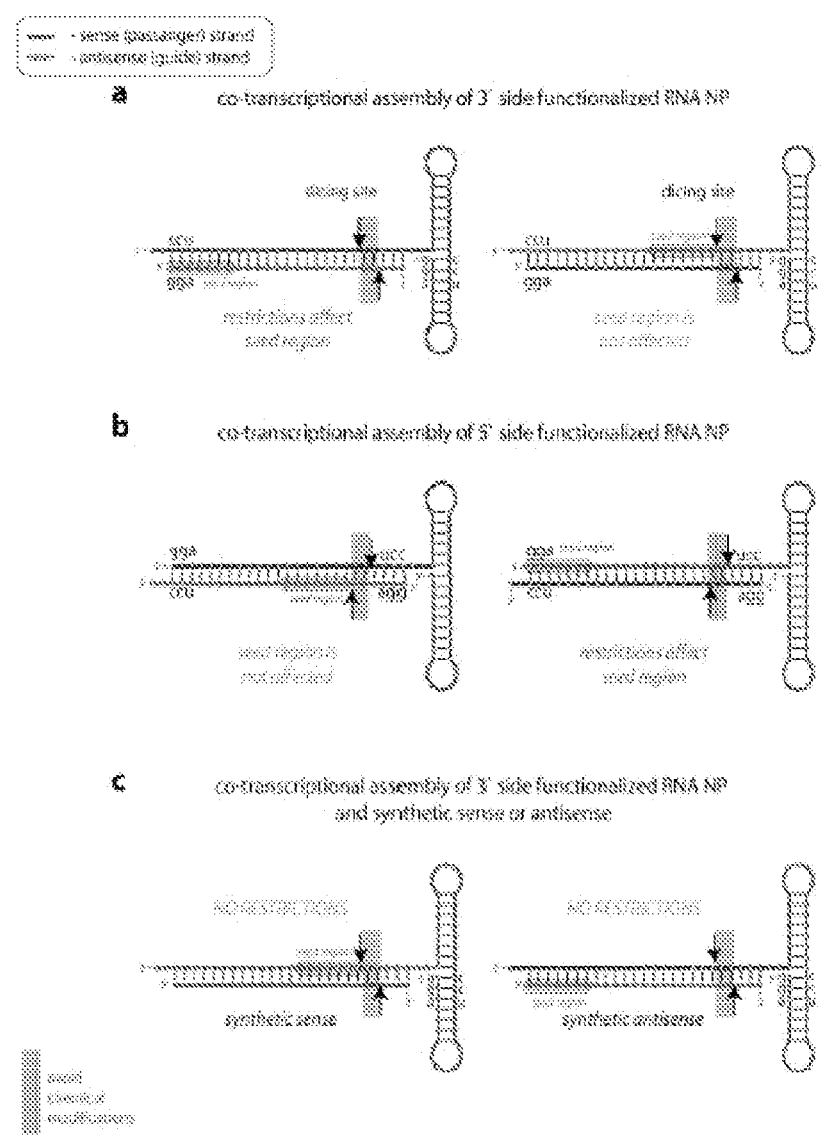
FIGS. 2A-2C illustrates structural sequence constraints applied to the design rules of co-transcriptionally assembling siRNA functionalized RNA NP due to the use of RNA starting sequences (e.g. 5'-gga) required for T7 RNA polymerase transcription initiation. All potential variants of starting sequences for high yield transcriptions with T7 RNA polymerase are listed elsewhere.

Example 1: High Yield Co-Assembly of RNA Nanoparticles Containing Modified Nucleotides Through the Use of Wild-Type T7 RNA Polymerase High yields of RNA NP were generated by eliminating the purification step of individual RNA strands and post-transcriptional assembly of RNA NPs. The methodology is based on in vitro transcription by wild type (wt) T7 RNA polymerase of a mixture of DNA templates encoding RNA strands that go into the composition of the given RNA NP (FIGS. 1 and 2). One illustrative example is the co-transcriptional assemblies of previously characterized RNA NPs: rings and cubes. These NPs were functionalized at either their 5'- or 3'-ends with siRNAs (0-6 siRNAs per RNA NP) targeted against green fluorescent protein (GFP). When all 6 siRNAs were present, the NPs were composed of 12 RNA strands each (FIGS. 3 and 4) (Afonin, K. A. et al., Nature protocols 2011, 6, (12), 2022-34). However, larger complexes are shown to be co-transcriptionally produced as well (e.g. RNA NP composed of 22 RNA strands shown in FIG. 5).

Figure 3:
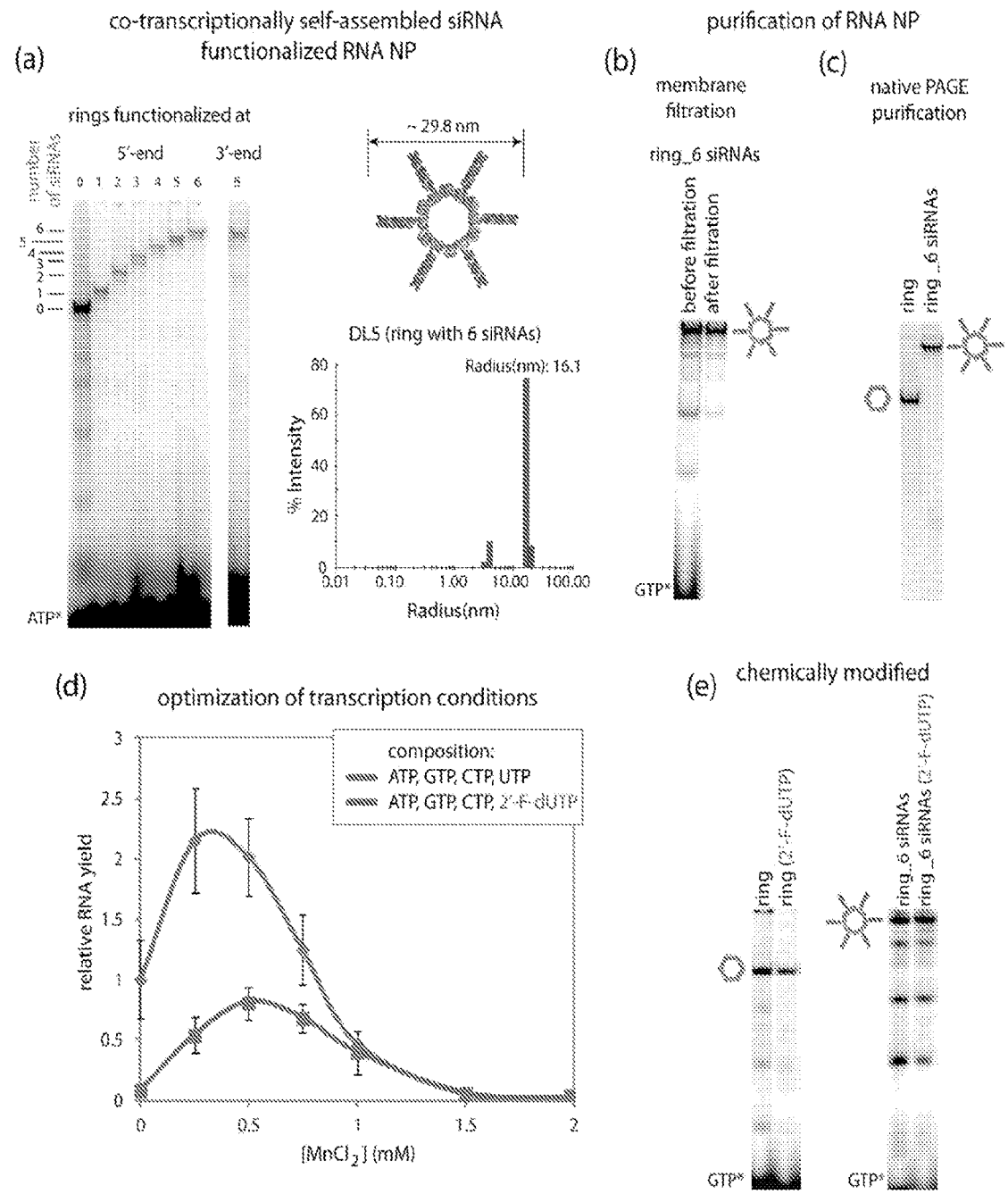
FIGS. 3A-3E shows the co-transcriptional assemblies of RNA nanoparticles (NP) with and without chemical modifications (2'-F-dUTP) and their further purifications.
Figure 4:
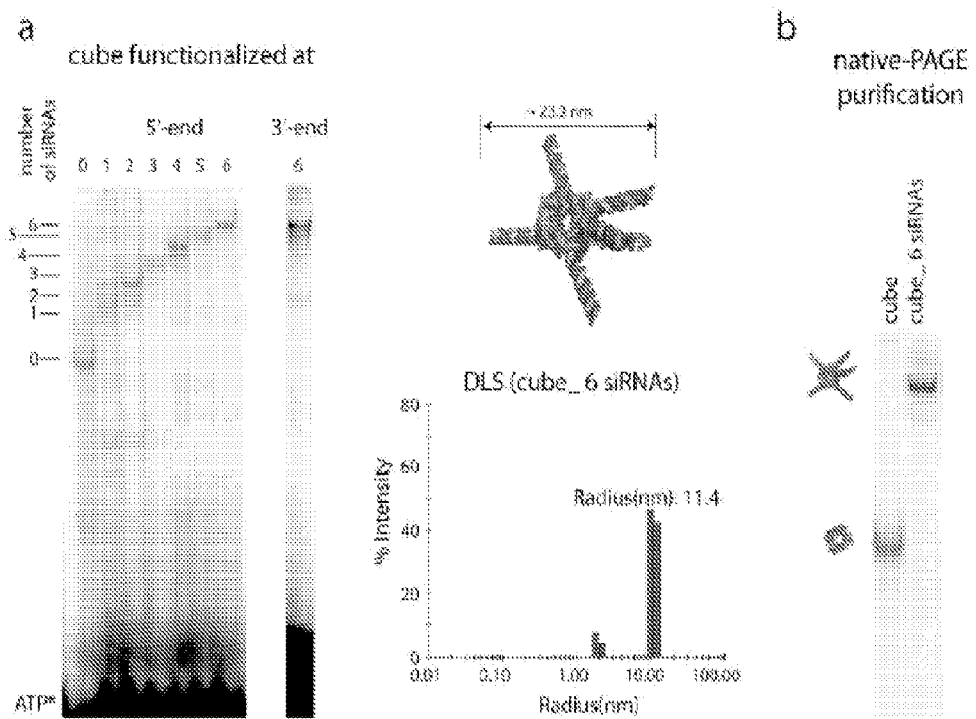
FIGS. 4A & 4B show co-transcriptional assemblies of 5'-side siRNA functionalized RNA NP of cubes.
Figure 5:
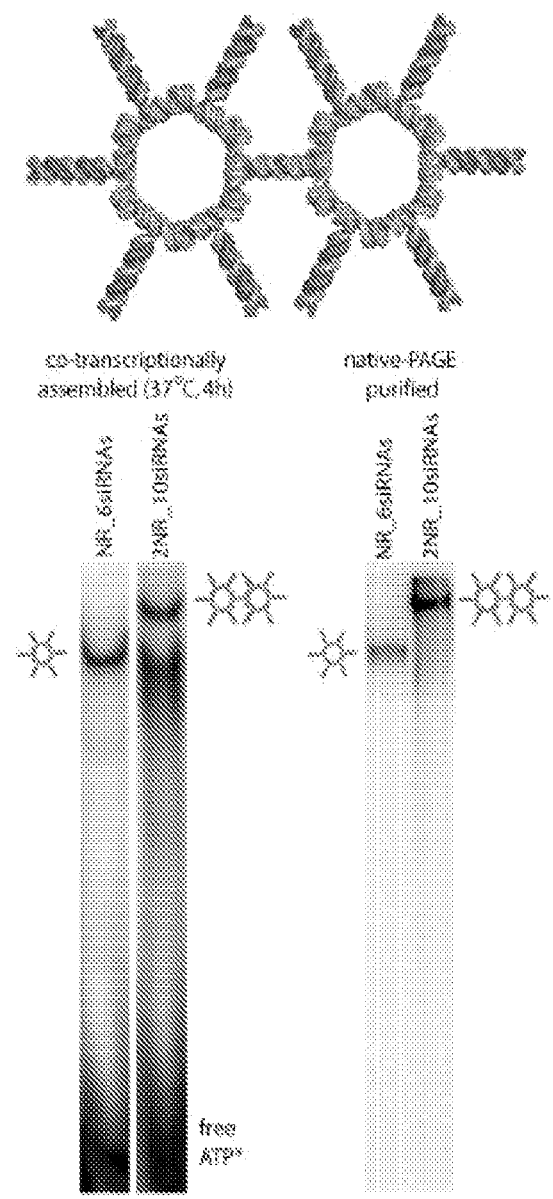
FIG. 5 shows the native PAGE characterization of co-transcriptionally assembled functionalized RNA NPs, composed of two nano-rings carrying 10 siRNAs, before and after gel purification.

Formation of RNA NP takes place directly in the transcription reaction when equimolar amounts of DNA templates encoding specifically designed RNAs (FIG. 2) are introduced. The resulting functional RNA NP, characterized by non-denaturing polyacrylamide gel electrophoresis (native PAGE) and dynamic light scattering (DLS) experiments (FIGS. 3 and 4), can be easily separated from other components of the transcription reaction by native PAGE or by membrane filtration (FIGS. 3 and 4). Furthermore, experimental conditions were established allowing for chemically modified RNA NP to be obtained with yields comparable to the non-modified RNAs (FIGS. 3 and 6) even when wt T7 RNA polymerase was used for transcription.

Substitution of UTPs with 2'-F-dUTPs in a conventional transcription buffer dramatically lowers the yields (more than 10-fold) of the transcribed full-length RNAs (FIG. 3 and supporting 6 at 0 mM $MnCl_2$). However, in the presence of $Mn^{2+}$, the production of chemically modified RNA molecules as well as co-transcriptionally assembled chemically modified RNA NP becomes possible in high yields with the wt T7 RNA polymerase. In the series of experiments addressing $Mn^{2+}$ effect on individual RNA strand synthesis (FIG. 3, blue curve), it was determined that the addition of 0.25-0.75 mM $Mn^{2+}$ to the transcription buffer containing 5 mM $MgCl_2$ and unmodified NTPs doubles the yield of RNA chains. Interestingly, the presence of $Mn^{2+}$ at 1 mM or higher concentrations had an inhibitory effect on transcription. When UTP was substituted with 2'-F-dUTP, $Mn^{2+}$ addition resulted in a >10-fold increase of the full-size chemically modified RNA yield (FIG. 3, red curve). The yields of the chemically modified RNAs in the presence of 5 mM $Mg^{2+}$ and 0.5 mM $Mn^{2+}$ were comparable to the unmodified RNAs transcribed in the presence of 5 mM $MgCl_2$. This result agrees with the previously reported effect of $Mn^{2+}$ on incorporation of 8-$N_3$AMP (Gopalakrishna, S. et al., Rna 2004, 10, (11), 1820-30). It appears that $Mn^{2+}$ relaxes the substrate specificity of T7 RNA polymerase in a manner similar to the Y639F mutation. However, in contrast to the Y639F mutation, $Mn^{2+}$ at 0.25-0.75 mM range promotes, rather than inhibits the transcription with regular NTP substrates. Notably, $Mn^{2+}$ does not interfere with the co-transcriptional assembly of RNA NP. Similar amounts of regular and chemically modified RNA NP were obtained in transcription reactions containing DNA templates encoding all chains required for the NP formation (FIG. 3). In some experiments, the yields of the chemically modified functionalized NPs appeared slightly higher than the yields of the unmodified NPs.

Figure 6:
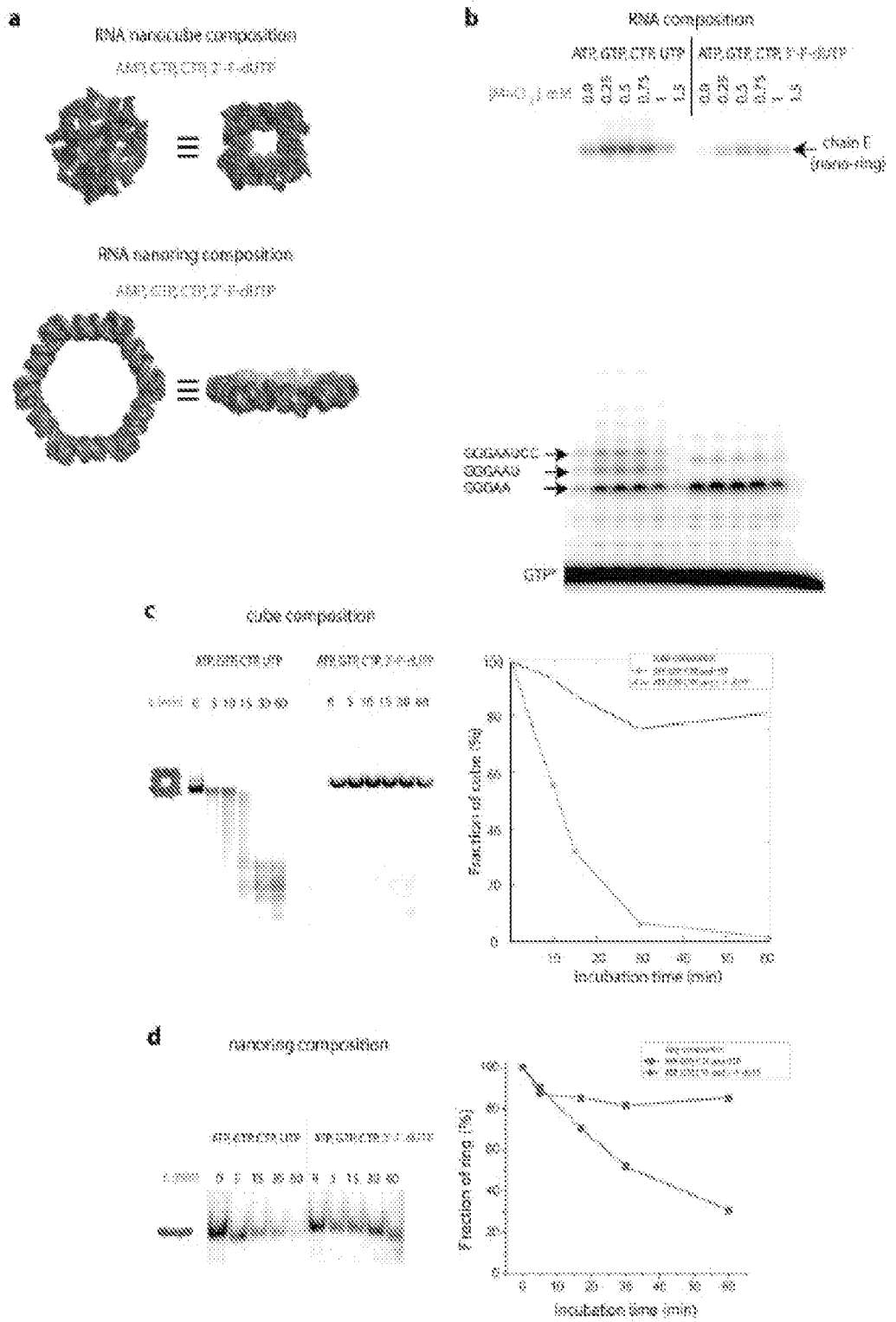
FIGS. 6A-6D show the co-transcriptionally assembled chemically modified (with 2'-F-dUTP) nano-cubes and nano-rings have higher stabilities in human blood serum compared to their non-modified analogs.
Figure 7:
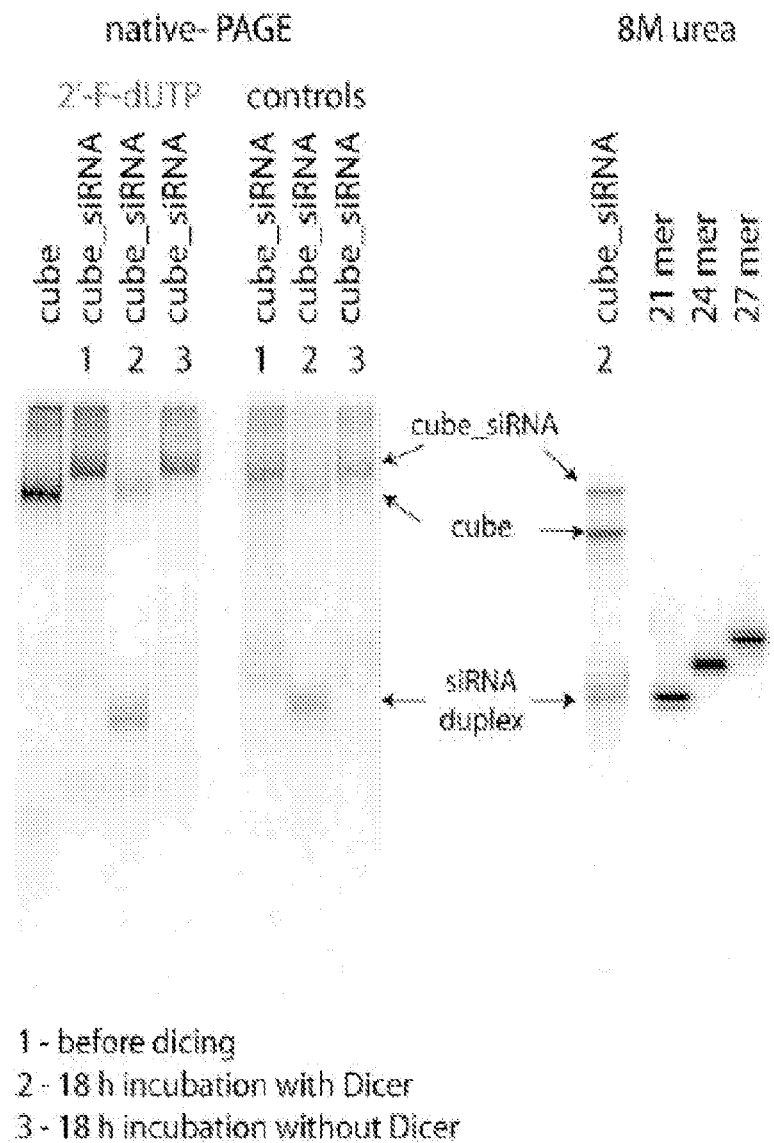
FIG. 7 shows the result of in vitro dicing experiments. Chemically modified with fluorinated uracils (2'-F-dUTP) functionalized with single siRNA nano-cubes were incubated with human recombinant dicer. The protocol is detailed elsewhere. The results were analyzed using native-PAGE and denaturing 8M urea PAGE techniques as described above. Non-modified RNA cubes were used as a control.

Replacement of UMP with 2'-F-dUMP in the RNA strands forming the nanocubes and nanorings results in increased resistance of the RNA NP to ribonucleases from human blood serum (FIG. 6). In addition to being significantly more resistant to blood serum ribonucleases, fluorinated RNA NP functionalized with siRNAs can still be processed by the human recombinant Dicer (FIG. 7).

Figure 8:
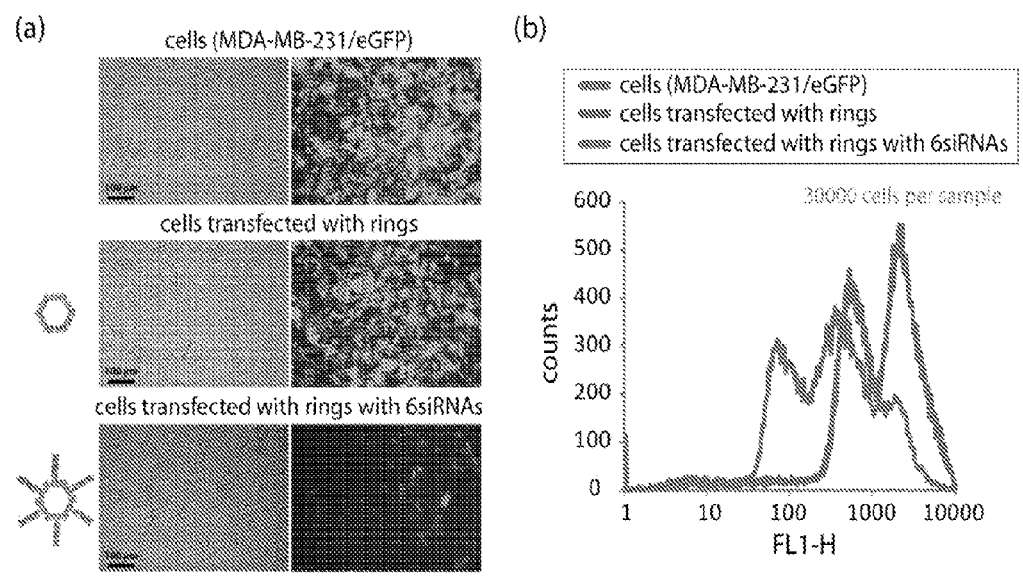
FIGS. 8A & 8B show GFP knockdown assays for human breast cancer cells (MDA-MB-231/GFP) which stably express enhanced GFP (eGFP). Three days after the transfection of cells with co-transcriptionally assembled RNA NP functionalized with siRNA against eGFP, eGFP expression was observed by (FIG. 8A) fluorescence microscopy and (FIG. 8B) statistically (30000 cells per sample) analyzed with flow cytometry experiments. Please note that the individual non-functionalized co-transcriptionally assembled RNA NP cause no decrease in eGFP production.
Figure 9:
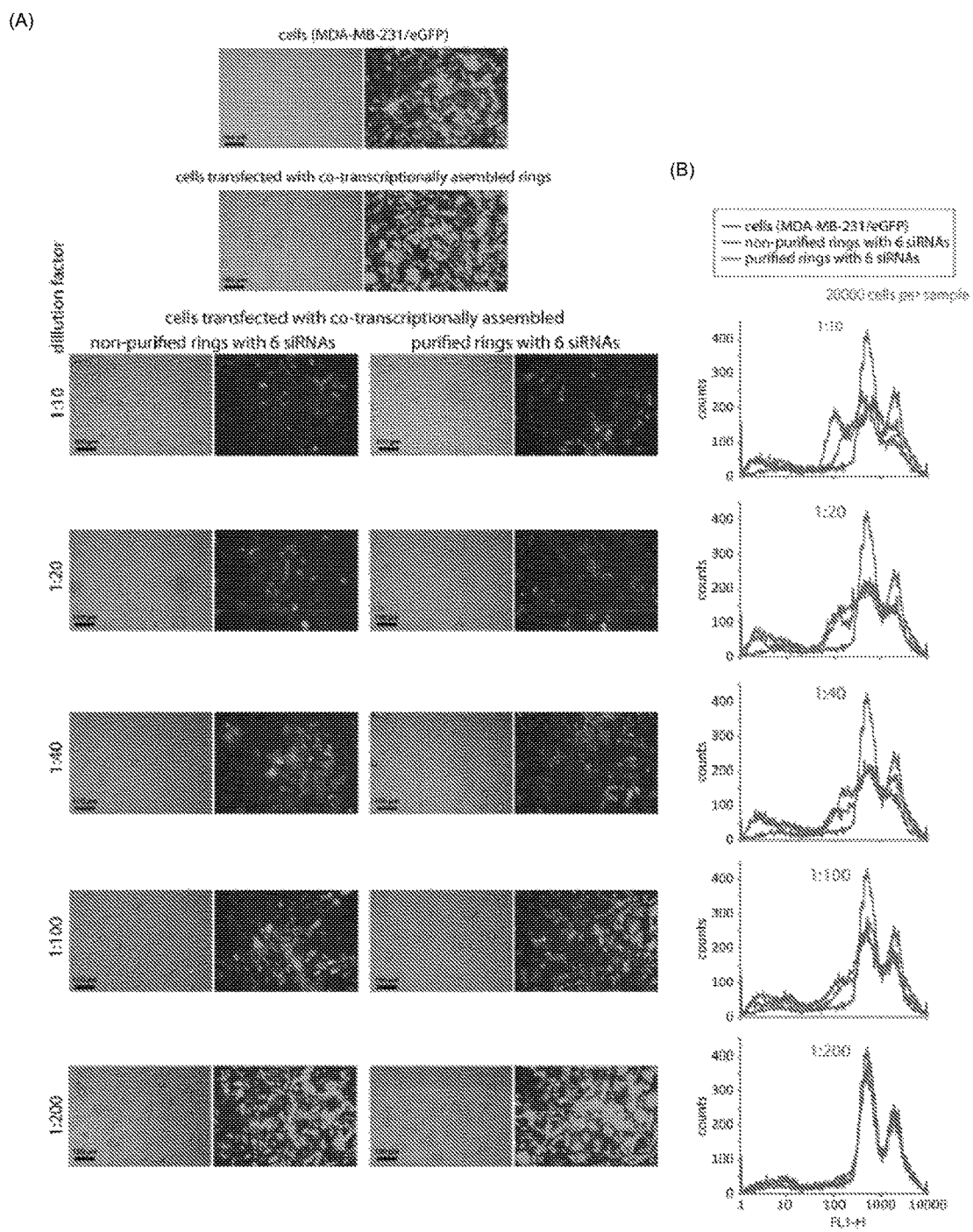
FIGS. 9A & 9B show GFP knockdown assays for human breast cancer cells (MDA-MB-231/GFP) which stably express enhanced GFP (eGFP) transfected with different amounts (dilutions) of purified and non-purified co-transcriptionally assembled rings functionalized with six siRNAs. Three days after the transfection of cells eGFP expression was observed by (FIG. 9A) fluorescence microscopy and (FIG. 9B) statistically (20000 cells) analyzed with flow cytometry experiments. Please note that at higher dilution, the non-purified RNA NP silence slightly better than the purified. This can be attributed to the relative loss of some material during the purification step.
Figure 10:
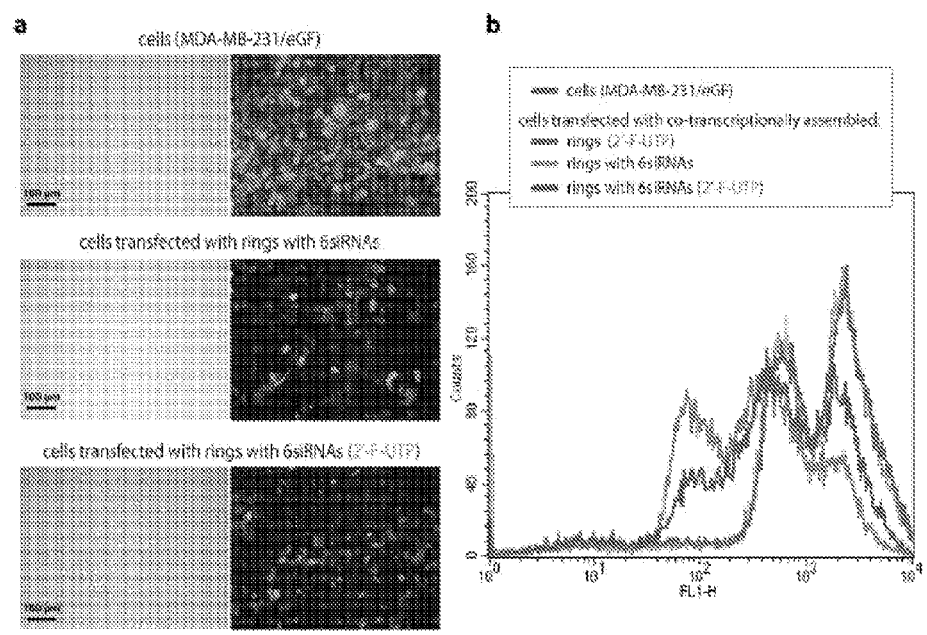
FIGS. 10A & 10B show GFP knockdown assays for human breast cancer cells (MDA-MB-231/GFP) which stably express enhanced GFP (eGFP) transfected (1:10 dilution) with chemically modified (2'-F-dUTP) rings functionalized with six siRNAs. Three days after the transfection of cells, eGFP expression was observed by (FIG. 10A) fluorescence microscopy and (FIG. 10B) statistically (30000 cells) analyzed with flow cytometry experiments. As the control, non-modified co-transcriptionally assembly was used.
Figure 11:
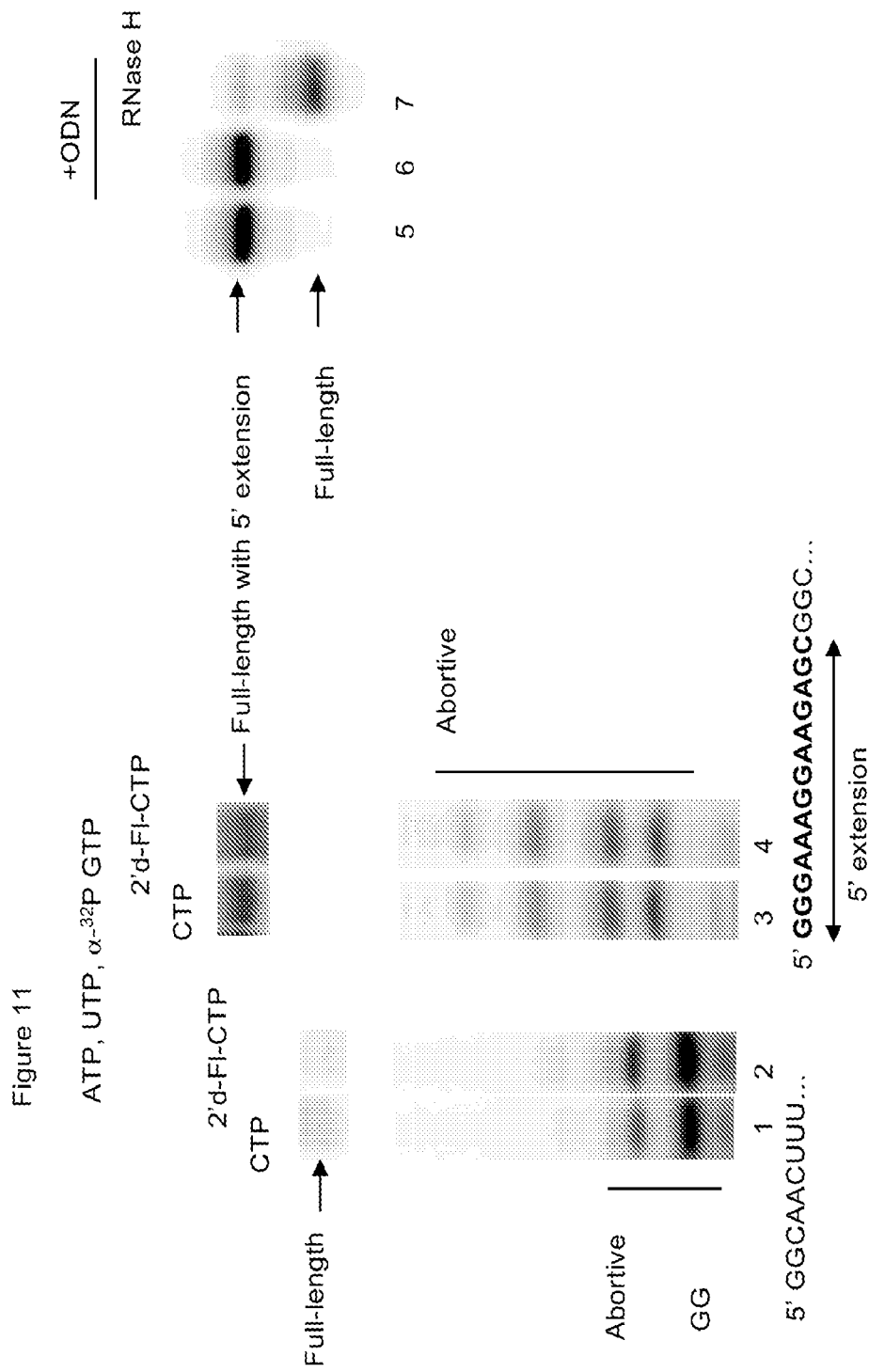
FIG. 11 shows the results of experiments using RNase H treatment.

Example 2: Transcription Reaction Mixtures Containing Non-Purified RNA NP are Functional In Vivo It is important to have "fast-screening" experiments to quickly assess the functionality of produced RNA NP. Therefore, we addressed if the transcription reaction mixtures containing non-purified RNA NP are suitable for functional cell culture assays (FIGS. 8 and 9) using human breast cancer cells stably expressing eGFP (MDA-MB-231/eGFP). In these experiments, cells were co-transfected with different amounts of purified and non-purified transcription mixtures and three days after, the level of eGFP expression was analyzed with fluorescence microscopy and flow cytometry. All experiments were repeated at least three times. The results demonstrated no eGFP silencing by the transcription mixture containing non-functionalized RNA NP. However, when the cells were transfected with the purified and non-purified co-transcriptionally assembled functionalized RNA NP, a significant level of silencing was detected even at the 100-fold dilution of initial transcription mixtures (FIGS. 8 and 9). Moreover, chemically modified (with 2'-F-dUMP) functionalized RNA NP caused significant silencing comparable to the non-modified RNA NP (FIG. 10). All these results are in a good agreement with silencing caused by in vitro assembled RNA NP and siRNA duplexes.

Example 3: Optimization of the RNA Yield by Addition of Oligopurine Tract at the 5'-End of the Transcript and RNase H-Mediated Removal of the Oligopurine Tract from the RNA Product Efficient co-transcriptional RNA NP assembly from several RNA molecules depends on coordinated expression of all the RNA strands of the nanoparticle. In the case of the nanocubes, the RNA 5' end sequences are essential for the NP formation, and the 5' end sequences vary in different RNA strands. At the same time, efficiency of transcription initiation and promoter escape of T7 RNAP strongly depends on the nature of the first few nucleotides of the transcribed sequence. For example, one of the nanocube strands showed very poor yields in the in vitro transcription compared to the strands of the nanoring and other strands of the nanocube. This strand starts with 5' GGCAACCUUU (SEQ ID NO: 1). Original template encoding strand A of the nanocube and the template carrying 12-bp insertion encoding the GGGAAAGGAAGAGC (SEQ ID NO: 2) sequence at the 5' end of the transcript were used for transcription with regular NTP mix (100 µM final) or with the NTP mix where CTP was substituted with 2'-d-Fl-CTP. The reaction conditions were the same as in the main protocol for co-transcriptional production of NP.

For ribonuclease H treatment, the transcription reaction was cooled to room temperature and 1 µM of the oligodeoxynucleotides and 0.01 u/µl E. coli ribonuclease H (Sigma) were added for 15 min.

The short abortive RNAs represent predominant products of transcription from this template (lane 1). Substitution of CTP with 2'-d-Fl CTP in the in vitro transcription reaction resulted in further decrease of the full-length RNA strand yield and the appearance of even higher amounts of the abortive initiation products (lane 2). Changes in $[Mn^{2+}]$ and $[Mg^{2+}]$ did not improve the full-length RNA yield. However, production of the full-length RNA strand dramatically increased when the original sequence was modified so that the resulting RNA strand was extended from the 5' end with the following sequence: 5' GGGAAAGGAAGAGC (SEQ ID NO: 2); the full-length RNA product is readily detectable when transcription is performed on the modified template, and the abortive products are no longer predominant (lane 3). Quantification of the bands and normalization to the amount of labeled GMP residues in each transcript suggests that the yields of the transcripts containing fluorinated dCMP (lane 4) and dUMP (not shown) increased 20-fold compared to the yields obtained with the original template. Apparently, the polypurine stretch decreases the propensity of T7 RNAP to undergo abortive initiation cycles. The synthesis of RNAs containing chemically modified pyrimidine residues is efficient on the template encoding the 5'-extended transcript, likely because the initiation to elongation transition occurs before the first modified residue has to be incorporated. Therefore, abortive transcription is not enhanced by the relatively slow incorporation of chemically modified analogues of CTP and UTP.

While 5' extension of the RNA strands dramatically increases the yield of the full-length product, it is also expected to interfere with the nanocube assembly. To resolve this problem and remove the extra RNA from the 5' end of the nanocube strand, 13-nt oligodeoxynucleotides complementary to the 5' end of the extended transcript were added (lane 6), and the resulting heteroduplex was treated with ribonuclease H. The treatment resulted in the removal of the 5' extension, and the appearance of the correct-size RNA product (lane 7). Notably, addition of the 13-nt sequence inhibits transcription, probably, by binding with T7 RNAP. Therefore, it should be added after transcription is completed.

The following modification to co-transcriptional assembly of RNA NP is proposed in case the yields of different RNA strands vary substantially:

All templates are modified by inserting 12 bp encoding GGGAAAGGAAGAG (SEQ ID NO: 3) sequence at the 5' end of the transcript.

One-pot transcription of the mixture of templates encoding all RNA strands of the NP is performed.

The reaction temperature is brought to 25° C. to promote hybridization to the RNA. The sequence complementary to the 5' extension and ribonuclease H are added.

The reaction temperature is brought to 37° C. to promote the NP folding.

The Above Examples were Carried Out Using the Following Materials and Methods.

RNA Sequence Design and Synthesis of the Corresponding DNA Templates.

RNA sequences used in this work and listed below have been designed and extensively characterized elsewhere (Afonin, K. A. et al., *Nat Nanotechnol* 5, 676-682 (2010); Afonin, K. A. et al., *Nature protocols* 6, 2022-2034 (2011); and Grabow, W. W. et al., *Nano Lett* 11, 878-887 (2011)). DNA templates used for PCR amplifications with corresponding primers containing the T7 RNA polymerase promoter region (20 nucleotides) were designed using the following link to the publically available software http://rna.bgsu.edu/oldwebsite/rnatodna.html. DNA oligonucleotides were purchased from IDT, the templates were generated by PCR and purified using the QIAquick PCR purification kit.

Co-Transcriptional Assemblies, Native PAGE Quality Control Experiments and Purification of Functional RNA NP.

The concentrations of amplified by PCR DNA template duplexes encoding the RNAs entering the composition of RNA NP were measured using NanoDrop 1000 spectrophotometer. Equimolar amounts of DNA templates were used for RNA synthesis and NP formation during transcription with T7 RNA polymerase. For assembly quality control and functional control dicing experiments, RNA molecules were labeled by α-[$^{32}$P]-GMP or α-[$^{32}$P]-AMP incorporation as detailed previously (Afonin, K. A. et al., *Nat Nanotechnol* 5, 676-682 (2010); and Afonin, K. A. et al., *Nature protocols* 6, 2022-2034 (2011)). Transcription was performed in 50 mM Tris-HCl, pH 7.6, 2 mM spermidine, 1 mM DTT, 0.4 units/µl RNasine (Promega), 5 mM $MgCl_2$, 0.5 mM $MnCl_2$, 100 µM NTP, 1-5 µCi α-[$^{32}$P] GTP, 0.01 µM of each template, and 0.3 units/µl T7 RNA polymerase (Promega) unless indicated otherwise. Analyses of the individual RNA strand transcription were performed in 20% (19:1) denaturing PAGE in the presence of 7M urea. Native PAGE experiments were performed as described (Afonin, K. A. et al., *Journal of the American Chemical Society* 130, 93-102 (2008); Afonin, K. A. et al., *Chembiochem: a European journal of chemical biology* 9, 1902-1905 (2008); and Afonin, K. A. & Leontis, N. B., *Journal of the American Chemical Society* 128, 16131-16137 (2006)) with appropriate control RNA NP assembled as detailed elsewhere (Afonin, K. A. et al., *Journal of the American Chemical Society* 130, 93-102 (2008)). Typically, co-transcriptional assembly experiments reported were analyzed at 10° C. in 7% (29:1) native polyacrylamide gels in the presence of 89 mM Tris-borate, pH 8.3, and 2 mM $Mg(OAc)_2$. An equal volume of loading buffer (same buffer with 0.01% bromphenol blue, 0.01% xylene cyanol, 50% glycerol) was added to each sample before loading on the native gel. Gels were run for 4 h at 25 W with the temperature set to 10° C., exposed to a phosphoimager screen for 30 minutes, and scanned using a Typhoon phosphoimager.

For partial purification of fully assembled RNA NP by centrifugal ultrafiltration the transcription mixture (after 4 hours incubation at 37° C.) was subjected to three cycles of dilution with 89 mM Tris-borate, pH 8.3, 2 mM $Mg(OAc)_2$ buffer containing 0.1 mg/ml BSA and concentration in the centrifugal filter device with a 100 kDa molecular weight cutoff membrane (Millipore). As an alternative, co-transcriptionally assembled RNA NP were gel-purified using native PAGE. The bands were visualized as described above, excised from the gel and eluted in 89 mM Tris-borate, pH 8.3, 2 mM $Mg(OAc)_2$ for 5 hours at 4° C.

Dynamic Light Scattering (DLS).

For DLS, 10 µl of sample solution containing co-transcriptionally assembled functionalized RNA NP were measured by DynaPro 99 (Protein Solution, Wyatt) with a laser wavelength of 824 nm at 24° C. The theoretical hydrodynamic radii (Rh) were calculated by measuring the distance between the center of mass and the farthest atom of the RNA NP three-dimensional CPK model.

Recombinant Human Dicer Assay.

Radiolabeled co-transcriptionally assembled RNA NPs were prepared as described above. For dicing experiments, samples were incubated for 4 hours at 37° C. with recombinant human turbo dicer enzyme kit (Genlantis), containing an ultra-active form of human recombinant dicer enzyme, according to the manufacturer's suggested protocol. Dicing reactions were quenched by adding dicer stop solution (provided by the manufacturer) prior to analysis on 2 mM $Mg(OAc)_2$ native 7% PAGE (described above) and denaturing 8M urea PAGE. In the case of denaturing 8M urea 7% PAGE, size markers (21-, 24-, and 27-mers) were used to confirm the dicing product.

Transfection of Human Breast Cancer Cells with Functional RNA NP.

For assaying the delivery of functional siRNA modified RNA NP, human breast cancer cell line MDA-MB-231 stably expressing eGFP was grown in D-MEM media (Gibco BRL) supplemented with 10% FBS and penicillin-streptomycin in a 5% $CO_2$ incubator. All transfections in this project were performed using commercially available Lipofectamine 2000 (L2K). Co-transcriptionally produced and column purified functional RNA NP were pre-incubated with L2K at 30° C. for 30 min. Prior to each transfection, the cell media was swapped with OPTI-MEM and prepared co-transcriptionally assembled RNA NP/L2K complexes were added. The cells were incubated for 4 hours followed by the media change (D-MEM, 10% FCS, 1% pen-strep).

Series of Dilutions Transfection Experiments.

Rings functionalized with six siRNAs were co-transcriptionally produced in total volume of 400 µl After that, the volume was split in two and 200 µl of mixture were column-purified, as described above. Resulting purified RNA NP were brought to the final volume of 200 µl with 89 mM Tris-borate, pH 7.4, 2 mM $Mg(OAc)_2$ buffer. For transfections, 100 µl, 50 µl, 25 µl, 10 µl, 5 µl of purified and non-purified co-transcriptional assembly mixtures were used to provide respectively 1:10, 1:20, 1:40, 1:100, 1:200 dilutions in OPTI-MEM (1 ml final, as described above). The cells were incubated for 4 hours followed by the media change (D-MEM, 10% FCS, 1% pen-strep).

Microscopy.

To assess the silencing efficiency, cells were imaged 72 hours after the transfection with a Nikon 200 TE inverted microscope (Melville, N.J.). We used a PanFluor 20×, ELWD, NA=0.45 objective and a Nikon B-2E/C, 465-495/505/515-555 cube for GFP imaging (Chroma Technology Corp., Rockingham, Vt.). MetaMorph software (Universal Imaging Co., Downingtown, Pa.) was used to operate the microscope.

Flow Cytometry.

For statistical analysis with flow cytometry experiments, the MDA-MB-231 (with eGFP) cells grown in 12-well plates ($10 \times 10^4$ cells per well) were lifted with cell dissociation buffer, washed twice with PBS and the level of expression of eGFP was determined by fluorescence-activated cell sorting (FACS) analysis on a FACScalibur flow cytometer (BD Bioscience). At least 20,000 events were collected and analyzed using the Cell quest software.

RNA Sequences Used in this Project

Cube Sequences

Letter sequences below the RNA strands indicate the desired interactions between different strands. Dots indicate the parts of the strands that are per design single-stranded. Sequence characters in lower letters were constrained to not change during the sequence optimization. RNAs were obtained by in vitro transcription of PCR generated DNA templates.

RNA cube scaffold strands
A (SEQ ID NO: 4)
ggcaacuuugaucccUCGGuuuagcgccGGCCuuuucucccACACuuuCACG

MMMMMM...KKKKKKLLLL...FFFFFFGGGG...BBBBBBCCCC...NNNN

B (SEQ ID NO: 5)
gggaaauuuCGUGGUAGGUuuuguugccCGUGuuuCUACGAUUACuuuGGUC

QQQQQQ...PPPPPPPPPP...MMMMMMNNNN...EEEEEEEEEE...RRRR

C (SEQ ID NO: 6)
ggacauuuuCGAGACAGCAuuuuuucccGACCuuuGCGGAUUGUAuUuUAGG

IIIIII...OOOOOOOOOO...QQQQQQRRRR...DDDDDDDDDD...JJJJ

D (SEQ ID NO: 7)
ggcgcuuuuGACCUUCUGCuuuaugucccCCUAuuuCUUAAUGACUuUuGGCC

FFFFFF...HHHHHHHHHH...IIIIIIJJJJ...AAAAAAAAAA...GGGG

E (SEQ ID NO: 8)
gggagauuuAGUCAUUAAGuuuUACAAUCCGCuuuGUAAUCGUAGuUuGUGU

BBBBBB...AAAAAAAAAA...DDDDDDDDDD...EEEEEEEEEE...CCCC

F (SEQ ID NO: 9)
gggaucuuuACCUACCACGuuuUGCUGUCUCGuuuGCAGAAGGUCuUuCCGA

KKKKKK...PPPPPPPPPP...OOOOOOOOOO...HHHHHHHHHH...LLLL

3' antisense siRNA (EGFPS1) modifications of RNA cubes with
10 bp perside and 3Us at the corners
A (SEQ ID NO: 10)
ggcaacuUugaucccUCGGuuUagcgccGGCCuUuucucccACACuUuCACGuuCGGUGGUGCAGAUGAACUUCAGGGUC MMMMMM...KKKKKKLLLL...FFFFFFGGGG...BBBBBBCCCC...NNNN..ZZZZZZZZZZZZZZZZZZZZZZZZZ..

B (SEQ ID NO: 11)
gggaaauUuCGUGGUAGGUuUuguugccCGUGuUuCUACGAUUACuUuGGUCuuCGGUGGUGCAGAUGAACUUCAGGGUC QQQQQQ...PPPPPPPPPP...MMMMMMNNNN...EEEEEEEEEE...RRRR..ZZZZZZZZZZZZZZZZZZZZZZZZZ..

C (SEQ ID NO: 12)
ggacauUuCGAGACAGCAuUuuuucccGACCuUuGCGGAUUGUAuUuUAGGuuCGGUGGUGCAGAUGAACUUCAGGGUC IIIIII...OOOOOOOOOO...QQQQQQRRRR...DDDDDDDDDD...JJJJ..ZZZZZZZZZZZZZZZZZZZZZZZZZ..

D (SEQ ID NO: 13)
ggcgcuuUuGACCUUCUGCuUuaugucccCCUAuUuCUUAAUGACUuUuGGCCuuCGGUGGUGCAGAUGAACUUCAGGGUC FFFFFF...HHHHHHHHHH...IIIIIIJJJJ...AAAAAAAAAA...GGGG..ZZZZZZZZZZZZZZZZZZZZZZZZZ..

E (SEQ ID NO: 14)
gggagauUuAGUCAUUAAGuUuUACAAUCCGCuUuGUAAUCGUAGuUuGUGUuuCGGUGGUGCAGAUGAACUUCAGGGUC BBBBBB...AAAAAAAAAA...DDDDDDDDDD...EEEEEEEEEE...CCCC..ZZZZZZZZZZZZZZZZZZZZZZZZZ..

F (SEQ ID NO: 15)
gggaucuUuACCUACCACGuUuUGCUGUCUCGuUuGCAGAAGGUCuUuCCGAuuCGGUGGUGCAGAUGAACUUCAGGGUC KKKKKK...PPPPPPPPPP...OOOOOOOOOO...HHHHHHHHHH...LLLL..ZZZZZZZZZZZZZZZZZZZZZZZZZ..

sense (SEQ ID NO: 16)
ggACCCUGAAGUUCAUCUGCACCACcg

..ZZZZZZZZZZZZZZZZZZZZZZZZZ

5' sense siRNA (EGFPS1) modifications of RNA cubes with
10 bp per side and 3Us at the corners
A (SEQ ID NO: 17)
ggcaagcugacccugaaguucauccaaggcaacuUugaucccUCGGuuUagcgccGGCCuUuucucccACACuUuCACG

ZZZZZZZZZZZZZZZZZZZZZZZZZZ..MMMMMM...KKKKKKLLLL...FFFFFFGGGG...BBBBBBCCCC...NNNN

B (SEQ ID NO: 18)
ggcaagcugacccugaaguucauccaagggaaauUuCGUGGUAGGUuUuguugccCGUGuUuCUACGAUUACuUuGGUC

ZZZZZZZZZZZZZZZZZZZZZZZZZZ..QQQQQQ...PPPPPPPPPP...MMMMMMNNNN...EEEEEEEEEE...RRRR

C (SEQ ID NO: 19)
ggcaagcugacccugaaguucauccaaggacauuUuCGAGACAGCAuUuuuucccGACCuUuGCGGAUUGUAuUuUAGG ZZZZZZZZZZZZZZZZZZZZZZZZZZZ..IIIIII...OOOOOOOOOO...QQQQQQRRRR...DDDDDDDDDD...JJJJ D (SEQ ID NO: 20)
ggcaagcugacccugaaguucauccaaggcgcuuUuGACCUUCUGCuUuaugucCCCUAuUuCUUAAUGACUuUuGGCC ZZZZZZZZZZZZZZZZZZZZZZZZZZZ..FFFFFF...HHHHHHHHHH...IIIIIIJJJJ...AAAAAAAAAA...GGGG E (SEQ ID NO: 21)
ggcaagcugacccugaaguucauccaagggagauUuAGUCAUUAAGuUuUACAAUCCGCuUuGUAAUCGUAGuUuGUGU ZZZZZZZZZZZZZZZZZZZZZZZZZZZ..BBBBBB...AAAAAAAAAA...DDDDDDDDDD...EEEEEEEEEE...CCCC F (SEQ ID NO: 22)
ggcaagcugacccugaaguucauccaagggaucuUuACCUACCACGuUuUGCUGUCUCGuUuGCAGAAGGUCuUuCCGA ZZZZZZZZZZZZZZZZZZZZZZZZZZZ..KKKKKK...PPPPPPPPPP...OOOOOOOOOO...HHHHHHHHHH...LLLL antisense (SEQ ID NO: 23)
GGATGAACTTCAGGGTCAGCTTGCCuu

ZZZZZZZZZZZZZZZZZZZZZZZZZZZ..

Ring Sequences
siRNA sequences used for NR modifications are identical to those used for the cubic NPs shown above. RNA sequences were obtained by in vitro transcription of PCR generated DNA templates.

```
RNA ring scaffold strands
A (SEQ ID NO: 24)
GGGAAUCCGUCCACUGGAUUCCCGUCACAGAGCCUGCCUGUGAC

B (SEQ ID NO: 25)
GGGAAUCCGCAGGCUGGAUUCCCGUCACAGAGAACGCCUGUGAC

C (SEQ ID NO: 26)
GGGAAUCCGCGUUCUGGAUUCCCGUCACAGACGUCUCCUGUGAC

D (SEQ ID NO: 27)
GGGAAUCCGAGACGUGGAUUCCCGUCACAGUCGUGGUCUGUGAC

E (SEQ ID NO: 28)
GGGAAUCCACCACGAGGAUUCCCGUCACAGAACCAUCCUGUGAC

F (SEQ ID NO: 29)
GGGAAUCCGAUGGUUGGAUUCCCGUCACAGAGUGGACCUGUGAC

3' antisense siRNA (EGFPS1) modifications of RNA rings
A (SEQ ID NO: 30)
GGGAACCGUCCACUGGUUCCCGCUACGAGAGCCUGCCUCGUAGCuuCGGUGGUGCAGAUGAACUUCAGGGUC B (SEQ ID NO: 31)
GGGAACCGCAGGCUGGUUCCCGCUACGAGAGAACGCCUCGUAGCuuCGGUGGUGCAGAUGAACUUCAGGGUC C (SEQ ID NO: 32)
GGGAACCGCGUUCUGGUUCCCGCUACGAGACGUCUCCUCGUAGCuuCGGUGGUGCAGAUGAACUUCAGGGUC D (SEQ ID NO: 33)
GGGAACCGAGACGUGGUUCCCGCUACGAGUCGUGGUCUCGUAGCuuCGGUGGUGCAGAUGAACUUCAGGGUC E (SEQ ID NO: 34)
GGGAACCACCACGAGGUUCCCGCUACGAGAACCAUCCUCGUAGCuuCGGUGGUGCAGAUGAACUUCAGGGUC F (SEQ ID NO: 35)
GGGAACCGAUGGUUGGUUCCCGCUACGAGAGUGGACCUCGUAGCuuCGGUGGUGCAGAUGAACUUCAGGGUC 5' sense siRNA (EGFPS1) modifications of RNA rings
A (SEQ ID NO: 36)
ggcaagcugacccugaaguucauccaaGGGAACCGUCCACUGGUUCCCGCUACGAGAGCCUGCCUCGUAGC B (SEQ ID NO: 37)
ggcaagcugacccugaaguucauccaaGGGAACCGCAGGCUGGUUCCCGCUACGAGAGAACGCCUCGUAGC
```

C (SEQ ID NO: 38)
ggcaagcugacccugaaguucauccaaGGGAACCGCGUUCUGGUUCCCGCUACGAGACGUCUCCUCGUAGC D (SEQ ID NO: 39)
ggcaagcugacccugaaguucauccaaGGGAACCGAGACGUGGUUCCCGCUACGAGUCGUGGUCUCGUAGC E (SEQ ID NO: 40)
ggcaagcugacccugaaguucauccaaGGGAACCACCACGAGGUUCCCGCUACGAGAACCAUCCUCGUAGC F (SEQ ID NO: 41)
ggcaagcugacccugaaguucauccaaGGGAACCGAUGGUUGGUUCCCGCUACGAGAGUGGACCUCGUAGC Sequences used to join two NRs together (complementary
joining sequences are underlined).
3'A_1 (SEQ ID NO: 42)
GGGAACCGUCCACUGGUUCCCGCUACGAGAGCCUGCCUCGUAGC<u>AAGGACCUACGACCUGACCUGUCC</u>

3'A_2 (SEQ ID NO: 43)
GGGAACCGUCCACUGGUUCCCGCUACGAGAGCCUGCCUCGUAGC<u>AAGGACAGGUCAGGUCGUAGGUCC</u>

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

---

What is claimed is:

1. A method of producing modified RNA nanoparticles comprising:
preparing a mixture comprising one or more dsDNA templates encoding a plurality of distinct RNA transcripts, wild-type T7 RNA polymerase, a modified nucleotide, and a buffer comprising manganese ions, and
incubating the mixture thereby transcribing the dsDNA templates to form the plurality of distinct RNA transcripts comprising the modified nucleotide, and
co-transcriptionally forming modified RNA nanoparticles by allowing the modified RNA transcripts to assemble without first separately purifying the modified RNA transcripts.

2. The method of claim 1, wherein modified RNA nanoparticles are nuclease resistant.

3. The method of claim 1, wherein the manganese ions are at from 0.25 mM to 0.75 mM.

4. The method of claim 1, wherein the manganese ions are at about 0.5 mM.

5. The method of claim 1, wherein the modified RNA nanoparticles comprise between 12 and 22 distinct RNA transcripts.

6. The method of claim 1, wherein the modified nucleotide comprises a modified nucleoside selected from the group consisting of 5-methylcytidine, 5-methyluridine, 2-thiouridine, $m^1A$ (1-methyladenosine); $m^2A$ (2-methyladenosine); Am (2'-O-methyladenosine); $ms^2$ $m^6A$ (2-methylthio-$N^6$-methyladenosine); $i^6A$ ($N^6$-isopentenyladenosine); $ms^2i6A$ (2-methylthio-$N^6$ isopentenyladenosine); $io^6A$ ($N^6$-(cis-hydroxyisopentenyl)adenosine); $ms^2i^6A$ (2-methylthio-$N^6$-(cis-hydroxyisopentenyl)adenosine); $g^6A$ ($N^6$-glycinylcarbamoyladenosine); $t^6A$ ($N^6$-threonylcarbamoyladenosine); $ms^2t^6A$ (2-methylthio-$N^6$-threonyl carbamoyladenosine); $m^6t^6A$ ($N^6$-methyl-$N^6$-threonylcarbamoyladenosine); $hn^6A$($N^6$-hydroxynorvalylcarbamoyladenosine); $ms^2hn^6A$ (2-methylthio-$N^6$-hydroxynorvalyl carbamoyladenosine); Ar(p) (2'-O-ribosyladenosine (phosphate)); I (inosine); $m^1I$ (1-methylinosine); $m^1Im$ (1,2'-O-dimethylinosine); $m^3C$ (3-methylcytidine); Cm (2'-O-methylcytidine); $s^2C$ (2-thiocytidine); $ac^4C$(N4-acetylcytidine); $f^5C$ (5-formylcytidine); $m^5$ Cm (5,2'-O-dimethylcytidine); $ac^4Cm$ ($N^4$-acetyl-2'-O-methylcytidine); $k^2C$ (lysidine); m1G (1-methylguanosine); $m^2G$ (N2-methylguanosine); $m^7G$ (7-methylguanosine); Gm (2'-O-methylguanosine); $m^2_2G$ ($N^2,N^2$-dimethylguanosine); $m^2Gm$ ($N^2$,2'-O-dimethylguanosine); $m^2_2Gm$ ($N^2,N^2$,2'-O-trimethylguanosine); Gr(p) (2'-O-ribosylguanosine (phosphate)); yW (wybutosine); $o_2yW$ (peroxywybutosine); OHyW (hydroxywybutosine); OHyW* (undermodified hydroxywybutosine); imG (wyosine); mimG (methylwyosine); Q (queuosine); oQ (epoxyqueuosine); galQ (galactosyl-queuosine); manQ (mannosyl-queuosine); $preQ_0$ (7-cyano-7-deazaguanosine); $preQ_1$ (7-aminomethyl-7-deazaguanosine); $G^+$ (archaeosine); D (dihydrouridine); $m^5Um$ (5,2'-O-dimethyluridine); $s^4U$ (4-thiouridine); $m^5s2U$ (5-methyl-2-thiouridine); $s^2Um$ (2-thio-2'-O-methyluridine); $acp^3U$ (3-(3-amino-3-carboxypropyl)uridine); $ho^5U$ (5-hydroxyuridine); $mo^5U$ (5-methoxyuridine); $cmo^5U$ (uridine 5-oxyacetic acid); $mcmo^5U$ (uridine 5-oxyacetic acid methyl ester); $chm^5U$ (5-(carboxyhydroxymethyl)uridine)); $mchm^5U$ (5-(carboxyhydroxymethyl)uridine methyl ester); $mcm^5U$ (5-methoxycarbonylmethyluridine); $mcm^5Um$ (5-methoxycarbonylmethyl-2'-O-methyluridine); $mcm^5s^2U$ (5-methoxycarbonylmethyl-2-thiouridine); $nm^5s2U$ (5-aminomethyl-2-thiouridine); $mnm^5U$ (5-methylaminoethyluridine); $mnm^5s^2U$ (5-methylaminomethyl-2-thiouridine); $mnm^5se2U$ (5-methylaminomethyl-2-selenouridine); $ncm^5U$ (5-carbamoylmethyluridine); $ncm^5Um$ (5-carbamoylmethyl-2'-O-methyluridine); $cmnm^5U$ (5-carboxymethylaminomethyluridine); $cmnm^5Um$ (5-carboxymethylaminomethyl-2'-O-methyluridine); $cmnm^5s2U$ (5-carboxymethylaminomethyl-2-thiouridine); m6$_2$A (N$^6$,N$^6$-dimethyladenosine); Im (2'-O-methylinosine); m$^4$C(N4-methylcytidine); m$^4$Cm (N$^4$,2'-O-dimethylcytidine); hm$^5$C (5-hydroxymethylcytidine); m$^3$U (3-methyluridine); cm$^5$U (5-carboxymethyluridine); m$^6$Am (N6,2'-O-dimethyladenosine); m$^6_2$Am (N$^6$,N$^6$,O-2'-trimethyladenosine); m$^2$,7G (N$^2$,7-dimethylguanosine); m$^2$,2,7G (N$^2$,N2,7-trimethylguanosine); m$^3$Um (3,2'-O-dimethyluridine); m$^5$D (5-methyldihydrouridine); f$^5$Cm (5-formyl-2'-O-methylcytidine); m$^1$Gm (1,2'-O-dimethylguanosine); m$^1$Am (1,2'-O-dimethyladenosine); τm$^5$U (5-taurinomethyluridine); τm$^5$s2U (5-taurinomethyl-2-thiouridine)); imG-14 (4-demethylwyosine); imG2 (isowyosine); and ac$^6$A (N6-acetyladenosine).

7. The method of claim 1, wherein the modified nucleotide is selected from the group consisting of 2'-fluoro-dUMP, 2'-fluoro-dCMP, 2'-fluoro-dGMP, and 2'-fluoro-dAMP.

8. The method of claim 1, wherein the modified nucleotide is 2'-fluoro-dUTP.

9. The method of claim 2, wherein the modified RNA nanoparticles having nuclease resistance have increased serum half-life compared to a corresponding RNA nanoparticles formed from wild-type RNA.

10. The method of claim 1, further comprising RNAse H treatment.

* * * * *

SEQUENCE LISTING

<160> NUMBER OF SEQ ID NOS: 44

<210> SEQ ID NO 1
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
ggcaaccuuu                                                              10

<210> SEQ ID NO 2
<211> LENGTH: 14
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
gggaaaggaa gagc                                                         14

<210> SEQ ID NO 3
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
gggaaaggaa gag                                                          13

<210> SEQ ID NO 4
<211> LENGTH: 52

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
ggcaacuuug aucccucggu uuagcgccgg ccuuucucc cacacuuuca cg            52

<210> SEQ ID NO 5
<211> LENGTH: 52
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
gggaaauuuc gugguagguu uuguugcccg uguuucuacg auuacuuugg uc            52

<210> SEQ ID NO 6
<211> LENGTH: 52
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
ggacauuuuc gagacagcau uuuucccga ccuuugcgga uuguauuuua gg            52

<210> SEQ ID NO 7
<211> LENGTH: 52
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
ggcgcuuuug accuucugcu uuaugucccc uauuucuuaa ugacuuuugg cc            52

<210> SEQ ID NO 8
<211> LENGTH: 52
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
gggagauuua gucauuaagu uuuacaaucc gcuuuguaau cguaguuugu gu            52

<210> SEQ ID NO 9
<211> LENGTH: 52
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
gggaucuuua ccuaccacgu uuugcugucu cguuugcaga aggucuuucc ga            52

<210> SEQ ID NO 10
<211> LENGTH: 80
<212> TYPE: RNA

<213> ORGANISM: Artificial Sequence
<220> FEATURE:
<223> OTHER INFORMATION: Description of Artificial Sequence: Synthetic oligonucleotide

<400> SEQUENCE: 10

```
ggcaacuuug aucccucggu uuagcgccgg ccuuuucucc cacacuuuca cguucggugg      60
ugcagaugaa cuucaggguc                                                 80
```

<210> SEQ ID NO 11
<211> LENGTH: 80
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 11

```
gggaaauuuc gugguagguu uuguugcccg uguuucuacg auuacuuugg ucuucggugg      60
ugcagaugaa cuucaggguc                                                 80
```

<210> SEQ ID NO 12
<211> LENGTH: 80
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 12

```
ggacauuuuc gagacagcau uuuuucccga ccuuugcgga uuguauuuua gguucggugg      60
ugcagaugaa cuucaggguc                                                 80
```

<210> SEQ ID NO 13
<211> LENGTH: 80
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 13

```
ggcgcuuuug accuucugcu uuauguccc uauuucuuaa ugacuuuugg ccuucggugg       60
ugcagaugaa cuucaggguc                                                 80
```

<210> SEQ ID NO 14
<211> LENGTH: 80
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 14

```
gggagauuua gucauuaagu uuuacaaucc gcuuuguaau cguaguuugu guucggugg       60
ugcagaugaa cuucaggguc                                                 80
```

<210> SEQ ID NO 15
<211> LENGTH: 80
<212> TYPE: RNA
<213> ORGANISM: Artificial Sequence
<220> FEATURE:
<223> OTHER INFORMATION: Description of Artificial Sequence: Synthetic oligonucleotide

```
<400> SEQUENCE: 15
gggaucuuua ccuaccacgu uuugcugucu cguuugcaga aggucuuucc gauucggugg    60
ugcagaugaa cuucaggguc                                                80

<210> SEQ ID NO 16
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
ggacccugaa guucaucugc accaccg                                        27

<210> SEQ ID NO 17
<211> LENGTH: 79
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
ggcaagcuga cccugaaguu cauccaaggc aacuuugauc ccucgguuua gcgccggccu    60
uuucucccac acuuucacg                                                 79

<210> SEQ ID NO 18
<211> LENGTH: 79
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
ggcaagcuga cccugaaguu cauccaaggg aaauuucgug guagguuuug uugcccgugu    60
uucuacgauu acuuugguc                                                 79

<210> SEQ ID NO 19
<211> LENGTH: 79
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
ggcaagcuga cccugaaguu cauccaagga cauuucgag acagcauuuu uucccgaccu    60
uugcggauug uauuuuagg                                                 79

<210> SEQ ID NO 20
<211> LENGTH: 79
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
ggcaagcuga cccugaaguu cauccaaggc gcuuugacc uucugcuuua uguccccuau    60
uucuuaauga cuuuuggcc                                                 79
```

<210> SEQ ID NO 21
<211> LENGTH: 79
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
ggcaagcuga cccugaaguu cauccaaggg agauuuaguc auuaaguuuu acaauccgcu    60
uuguaaucgu aguuugugu                                                79

<210> SEQ ID NO 22
<211> LENGTH: 79
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
ggcaagcuga cccugaaguu cauccaaggg aucuuuaccu accacguuuu gcugucucgu    60
uugcagaagg ucuuuccga                                                79

<210> SEQ ID NO 23
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 23
ggatgaactt cagggtcagc ttgccuu                                       27

<210> SEQ ID NO 24
<211> LENGTH: 44
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
gggaauccgu ccacuggauu cccgucacag agccugccug ugac                    44

<210> SEQ ID NO 25
<211> LENGTH: 44
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
gggaauccgc aggcuggauu cccgucacag agaacgccug ugac                    44

<210> SEQ ID NO 26
<211> LENGTH: 44
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 26
gggaauccgc guucuggauu cccgucacag acgucuccug ugac                           44

<210> SEQ ID NO 27
<211> LENGTH: 44
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 27
gggaauccga gacguggauu cccgucacag ucguggucug ugac                           44

<210> SEQ ID NO 28
<211> LENGTH: 44
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 28
gggaauccac cacgaggauu cccgucacag aaccauccug ugac                           44

<210> SEQ ID NO 29
<211> LENGTH: 44
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 29
gggaauccga ugguuggauu cccgucacag aguggaccug ugac                           44

<210> SEQ ID NO 30
<211> LENGTH: 72
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 30
gggaaccguc cacugguucc cgcuacgaga gccugccucg uagcuucggu ggugcagaug          60
aacuucaggg uc                                                             72

<210> SEQ ID NO 31
<211> LENGTH: 72
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 31
gggaaccgca ggcugguucc cgcuacgaga gaacgccucg uagcuucggu ggugcagaug          60
aacuucaggg uc                                                             72

<210> SEQ ID NO 32
<211> LENGTH: 72

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
gggaaccgcg uucugguucc cgcuacgaga cgucccucg uagcuucggu ggugcagaug      60
aacuucaggg uc                                                         72

<210> SEQ ID NO 33
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
gggaaccgag acgugguucc cgcuacgagu cguggucucg uagcuucggu ggugcagaug      60
aacuucaggg uc                                                         72

<210> SEQ ID NO 34
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
gggaaccacc acgagguucc cgcuacgaga accauccucg uagcuucggu ggugcagaug      60
aacuucaggg uc                                                         72

<210> SEQ ID NO 35
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
gggaaccgau gguugguucc cgcuacgaga guggaccucg uagcuucggu ggugcagaug      60
aacuucaggg uc                                                         72

<210> SEQ ID NO 36
<211> LENGTH: 71
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
ggcaagcuga cccugaaguu cauccaaggg aaccguccac ugguucccgc uacgagagcc      60
ugccucguag c                                                          71

<210> SEQ ID NO 37
<211> LENGTH: 71
<212> TYPE: RNA
<213> ORGANISM: Artificial Sequence
<220> FEATURE:
<223> OTHER INFORMATION: Description of Artificial Sequence: Synthetic
```

-continued oligonucleotide

<400> SEQUENCE: 37
ggcaagcuga cccugaaguu cauccaaggg aaccgcaggc ugguucccgc uacgagagaa    60
cgccucguag c    71

<210> SEQ ID NO 38
<211> LENGTH: 71
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
ggcaagcuga cccugaaguu cauccaaggg aaccgcguuc ugguucccgc uacgagacgu    60
cuccucguag c    71

<210> SEQ ID NO 39
<211> LENGTH: 71
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
ggcaagcuga cccugaaguu cauccaaggg aaccgagacg ugguucccgc uacgagucgu    60
ggucucguag c    71

<210> SEQ ID NO 40
<211> LENGTH: 71
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
ggcaagcuga cccugaaguu cauccaaggg aaccaccacg agguucccgc uacgagaacc    60
auccucguag c    71

<210> SEQ ID NO 41
<211> LENGTH: 71
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
ggcaagcuga cccugaaguu cauccaaggg aaccgauggu ugguucccgc uacgagagug    60
gaccucguag c    71

<210> SEQ ID NO 42
<211> LENGTH: 68
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42

```
gggaaccguc cacugguucc cgcuacgaga gccugccucg uagcaaggac cuacgaccug    60
accugucc                                                             68

<210> SEQ ID NO 43
<211> LENGTH: 68
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
gggaaccguc cacugguucc cgcuacgaga gccugccucg uagcaaggac aggucagguc    60
guaggucc                                                             68

<210> SEQ ID NO 44
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
gggaaaggaa gagcggc                                                   17
```